US009055721B2

(12) United States Patent
Mei et al.

(10) Patent No.: US 9,055,721 B2
(45) Date of Patent: Jun. 16, 2015

(54) METHODS AND MEDIA FORMULATIONS FOR LARGE-SCALE AND EFFICIENT MICROPROPAGATION OF BIO-ENERGY GRASSES

(75) Inventors: Chuansheng Mei, Danville, VA (US); Seonhwa Kim, Danville, VA (US); Kedong Da, Danville, VA (US)

(73) Assignee: THE INSTITUTE FOR ADVANCED LEARNING AND RESEARCH VA (US)

( * ) Notice: Subject to any disclaimer, the term of this patent is extended or adjusted under 35 U.S.C. 154(b) by 515 days.

(21) Appl. No.: 13/183,992

(22) Filed: Jul. 15, 2011

(65) Prior Publication Data

US 2012/0042569 A1 Feb. 23, 2012

Related U.S. Application Data

(60) Provisional application No. 61/375,223, filed on Aug. 19, 2010, provisional application No. 61/415,068, filed on Nov. 18, 2010.

(51) Int. Cl.
 *A01H 4/00* (2006.01)
(52) U.S. Cl.
 CPC ................ *A01H 4/005* (2013.01); *A01H 4/008* (2013.01)
(58) Field of Classification Search
 CPC ............................. A01H 4/005; A01H 4/008
 USPC ............................................ 435/430.1; 47/59
 See application file for complete search history.

(56) References Cited

U.S. PATENT DOCUMENTS

| | | | |
|---|---|---|---|
| 2,821,782 | A | 2/1958 | Kallweit |
| 4,666,844 | A | 5/1987 | Cheng |
| 4,684,612 | A | 8/1987 | Hemphill et al. |
| 4,837,152 | A | 6/1989 | Hemphill et al. |
| 5,183,757 | A | 2/1993 | Roberts |
| 5,294,549 | A | 3/1994 | Pullman et al. |
| 5,445,961 | A | 8/1995 | Genovesi et al. |
| 5,840,581 | A | 11/1998 | Carraway et al. |
| 5,908,771 | A | 6/1999 | Liu et al. |
| 6,071,746 | A | 6/2000 | Seabrook et al. |
| 6,555,375 | B1 | 4/2003 | Golovko |
| 6,677,154 | B2 | 1/2004 | Gielis et al. |
| 6,682,931 | B2 | 1/2004 | Becwar et al. |
| 6,821,782 | B2 | 11/2004 | Marton et al. |
| 6,995,016 | B2 | 2/2006 | Eudes et al. |
| 7,052,912 | B1 | 5/2006 | Woods et al. |
| 7,102,056 | B1 | 9/2006 | Lemaux et al. |
| 7,238,862 | B2 | 7/2007 | Allison et al. |
| 7,303,916 | B2 | 12/2007 | Marton et al. |
| 7,402,433 | B2 | 7/2008 | Sharon et al. |
| 7,445,932 | B2 | 11/2008 | Kumar et al. |
| 7,625,754 | B2 | 12/2009 | Gupta et al. |
| 2002/0166149 | A1 | 11/2002 | Marton et al. |
| 2003/0110531 | A1 | 6/2003 | Dan et al. |
| 2008/0282424 | A1 | 11/2008 | Marton et al. |

FOREIGN PATENT DOCUMENTS

| | | |
|---|---|---|
| CN | 101248756 | 8/2008 |
| CN | 101352147 | 1/2009 |
| WO | WO 2008/136797 | 11/2008 |
| WO | WO 2009/132116 | 10/2009 |
| WO | WO 2010/011717 | 1/2010 |

OTHER PUBLICATIONS

Sarada et al. Multiple Shoot Induction from Immature inflorescence in Shorghum. Cytologia 68(2) 199-204 2003.*
Arjumand et al. Optimization of the protocols for callus induction regeneration and acclimatization of sugar cane cv. thatta-10. Pak. J. Bot. 41(2) 815-820.2009.*
Sanchez et al. Requirement for invitro rooting of *Quercus robur* and *Q rubra* shoots derived from mature trees. Trees physiology 16 673-680 1996.*
Pulli et al. Biotechnical Improvement in Timothy Breeding http://www.internationalgrasslands.org/files/igc/publications/2001/id1210.pdf.*
Clifton-Brown, et al., "*Overwintering problems of newly established Miscanthus plantations can be overcome by identifying genotypes with improved rhizome cold tolerance*"; Research New Phytol. vol. 148, pp. 287-294, (2000).
Dohleman and Long, "*More Productive Than Maize in the Midwest: How does Miscanthus Do it?*", Plant Physiology, American Society of Plant Biologists, vol. 150, pp. 2104-2115, ( Aug. 2009).
Glowacka, et al., *The effects of genotype, inflorescence developmental stage and induction medium on callus induction and plant regeneration in two Miscanthus species*; Plant Cell Tiss Organ Cult. © Springer Science+Business Media B.V., vol. 102, doi: 10.1007/s11240-010-9708-6, pp. 79-86, (2010).
Heaton et.al., "*A quantitative review comparing the yields of two candidate $C_4$ perennial biomass crops in relation to nitrogen, temperature and water*", Biomas Bioenergy, Science Direct; vol. 27, pp. 21-30, (2004).
Holme et.al., "*Embryogenic callus formation, growth and regeneration in callus* and suspension cultures of *Miscanthus* X ogiformis Honda Giganteus' as affected by proline" Plant Cell Tissue Organ Cult, pp. 203-210, vol. 50, (1997).

(Continued)

*Primary Examiner* — Annette Para
(74) *Attorney, Agent, or Firm* — Novak Druce Connolly Bove + Quigg LLP

(57) ABSTRACT

A system, method and media formulation for high-quality and large-scale micropropagation of graminaceous plants such as *M.×giganteus* and switchgrass have been developed and include callus induction, callus propagation, plantlet regeneration, shoot multiplication, shoot quality improvement and rooting, resulting in high plant survival in the greenhouse and in the field. The systems and methods described herein are theoretically capable of producing more than 700 billion plants from one single shoot in one year.

13 Claims, 11 Drawing Sheets

(56) References Cited

OTHER PUBLICATIONS

Holme, et al., "*Callus Induction and plant regeneration from different explant types* of *Miscanthus* X ogiformis Honda 'Giganteus'", Plant Cell, Tissue and Organ Culture, vol. 45, pp. 43-52, (1996).

Holme, et al., *Growth Characteristics and nutrient depletion of Miscanthus x ogiformis Honda 'Giganteus' suspension cultures*, Plant Cell, Tissue and Organ Culture, vol. 53, pp. 143-151 (1998).

Jakob, et al., *Genetic improvement of C4 grasses as cellulosic biofuel feedstocks*, In Vitro Cell Development Biol.—Plant, vol. 45; pp. 291-305 (2009).

Kim, et al., "*Miscanthus x giganteus plant regeneration: effect of callus types, ages and culture methods on regeneration competence*", Global Change Biology Bioenergy, Blackwell Publishing Ltd, vol. 2, pp. 192-200, doi: 10.1111/j.1757.2010.01054.x, (2010).

Lewandowski, *Micropropagation of Miscanthus x giganteus*, Biotechnology in Agriculture and Forestry, High-Tech and Micropropagation V (ed. By Y.P.S. Bajaj), © Springer-Verlag Berlin Heidelberg, vol. 39, pp. 240-255, (1997).

Lewandowski, *Propagation method as an important factor in the growth and development of Miscanthus x giganteus*, Elsevier Science B.V., Industrial Crops and Products an International Journal, vol. 8, pp. 229-245, (1998).

Lewandowski, et al., "*Miscanthus: European experience with a novel energy crop*", Biomass and Bioenergy, vol. 19, pp. 209-227, (2000).

Lewandowski, et al., "*The development and current status of perennial rhizomatous grasses as energy crops in the US and Europe*", Science Direct, Biomass & Bioenergy; vol. 25, pp. 335-361 (2003).

Mani, Sarada et.al., Multiple shoot induction from immature inflorescence in Sorghum, (abstract), Cytologia, vol. 68, 2003:199-204.

Mei, Chuansheng et.al., A high Efficient System for Micropropagation of Large-Scale and High-Quality *Miscanthus* x giganteus plants.

Nielsen, et al., *Synergism of thidiazuron and benzyladenine in axillary shoot formation depends on sequence of application in Miscanthus X ogiformis 'Giganteus'*; Plant Cell, Tissue and Organ Culture, © Kluwer Academic Publishers, vol. 41, pp. 165-170, (1995).

Petersen, "*Callus induction and plant regeneration in Miscanthus x ogiformis Honda 'Giganteus' as influenced by benzyladenine*", Plant Cell, Tissue and Organ Culture, vol. 49, pp. 137-140 (1997).

Petersen, et al., *Significance of different carbon sources and sterilization methods on callus induction and plant regeneration of Miscanthus x ogiformis Honda 'Giganteus'*, Plant Cell, Tissue and Organ Culture, © Kluwer Academic Publishers, vol. 58, pp. 189-197, (1999).

Salvi, Neeta D., et.al., Direct regeneration of shoots from immature inflorescence cultures of turmeric, Journal Article (abstract), vol. 62, (2000): pp. 235-238.

Seonhwa Kim, Kedong Da, and Chuansheng Mei, P-2031, "A High Efficient System for Micropropagation of Large-Scale and High-Quality Miscanthus x giganteus Plants", Plant Posters, 2011 In Vitro Biology Meeting Abstract Issue, In Vitro Cell. Dev.Biol.—Animal, DOI 10,1007/s11626-011-9414-7, published Apr. 27, 2011, publication of poster first presented Mar. 26, 2010.

\* cited by examiner

FIG. 1. Diagram for Micropropagation Protocol

METHODS AND MEDIA FORMULATIONS FOR LARGE-SCALE AND EFFICIENT MICROPROPAGATION OF BIO-ENERGY GRASSES

CROSS REFERENCE TO RELATED APPLICATIONS

This claims priority from U.S. Provisional application No. 61/375,223 filed Aug. 19, 2010 and U.S. provisional patent application No. 61/415,068 filed Nov. 18, 2010, each incorporated herein by reference in its entirety.

GOVERNMENT SPONSORED RESEARCH

This invention was made with government support under USDA-NIFA Award #2009-38891-20092 to the Advanced Institute of Advanced Learning and Research awarded by the United States Department of Agriculture. The government has certain rights in the invention

FIELD OF THE INVENTION

The invention relates generally to media, systems, and methods for large-scale micropropagation of commercial crop plants such as *Miscanthus×giganteus* (*Miscanthus*) and *Panicum virgatum* L. (switchgrass).

BACKGROUND

*M.×giganteus* is a tall, warm-season perennial grass, which has been grown in Europe as a biofuel and bioenergy crop for more than a decade. It is a sterile triploid (3N=57) generated from the hybridization of the diploid *M. sinensis* (2N=38) with the tetraploid *M. sacchariflorus* (4N=76) and is characterized as a low input and low maintenance plant with a high yield, little or no susceptibility to pests and diseases, and low moisture and low ash contents at harvest. In comparison with switchgrass, it was reported that *M.×giganteus* produced 2 times more biomass than switchgrass (Heaton et al., Biomass Bioenergy vol. 27:21-30, 2004). Also, *M.×giganteus* produces approximately 2.5 times the amount of ethanol than corn does. It has a great leaf area and a long growing season, and can thus gain a great amount of photosynthetic carbon per unit of leaf area (Dohleman and Long, Plant Physiol. vol. 150:2104-2115, 2009). It has been considered as one of the most promising biofuel and bioenergy crops in the US and as an ideal plant for producing fuel ethanol at a lower cost than corn.

*M.×giganteus* is a sterile hybrid and does not produce viable seeds so it has not been found to be invasive in Europe or the United States. However, plants can only be propagated from rhizomes or through tissue culture-based micropropagation. The cost for producing plants from rhizomes is expensive and low-throughput, yielding low numbers of plants. Hence, more practical and high-throughput protocols are needed to provide the large number of plants for the large-scale plantings required to make this a viable energy crop in the US. In Europe, almost all plants are produced by micropropagation, as plants from rhizome division are too expensive and the propagation rate relatively low (Lewandowski, Micropropagation of *Miscanthus×giganteus*. In: Biotechnology in Agriculture and Forest, ed. By Bajaj YPS, Springer-Verlag Berlin Heidelberg. Vol. 39: p240-255, 1997).

SUMMARY

Described herein are systems, methods, and media formulations for large-scale propagation of a graminaceous grass, such as *Miscanthus* or switchgrass. *M.×giganteus* is considered one of the most promising biofuel and bioenergy crops. It is a perennial grass, has a high biomass yield, and requires fewer inputs, such as fertilizers and pesticides. However, it is a triploid hybrid and cannot produce viable seeds. Although there are protocols for micropropagation used in Europe, the multiplication rate and plant quality need to be improved for commercialization in order to meet market demand. A novel system, method and media formulations for high-quality and large-scale micropropagation of *M.×giganteus* have been developed, which includes callus induction, callus propagation, plantlet regeneration, shoot multiplication, shoot quality improvement and rooting, resulting in 99% of plant survival in the greenhouse and in the field. Novel media formulations for callus induction and multiplication, plantlet regeneration, rooting, shoot multiplication and shoot quality improvement have been developed and are described herein. The systems and methods described herein are theoretically capable of producing more than 700 billion plants from one single shoot in one year. The highly efficient tissue culture micropropagation system described herein may substantially reduce the cost of micropropagation of *Miscanthus* and other plants.

Accordingly, described herein is a method of propagating a graminaceous plant. The method includes the steps of: using immature inflorescence as explains to induce embryogenic calli; performing callus multiplication in liquid suspension medium or on solid medium; regenerating plantlets from embryogenic calli on regeneration medium; culturing the plantlets in liquid shoot multiplication media for shoot multiplication resulting in an increased number of shoots; culturing the plantlets in liquid shoot quality improvement media for shoot quality improvement resulting in a further increased number of shoots and an increase in shoot diameter; and transferring the plantlets to liquid rooting medium including activated charcoal. The graminaceous plant can be, for example, switchgrass, transgenic switchgrass, *Miscanthus*, transgenic *Miscanthus*, and chromosome-doubled *Miscanthus*, or other grass plant. The step of using immature inflorescence as explants to induce embryogenic calli can include washing, sterilizing, and culturing the immature inflorescence in callus induction medium, e.g., CIM2, CIM3, CIM4, CIM5, and CIM6 as listed in TABLE 1. The step of performing callus multiplication in liquid suspension medium or on solid medium can include culturing induced calli from the step of using immature inflorescence as explants to induce embryogenic calli in suspension culture medium SCM4 as listed in TABLE 2. The regeneration medium can be, for example, RM4 as listed in TABLE 3. The liquid shoot multiplication media can be any of SMM2, SMM3, SMM4, SMM5, SMM6, and SMM7 as listed in TABLE 4 and SMM5-1, 5-2, as listed in TABLE 5. The liquid shoot quality improvement media can be, for example, SQM4 as listed in TABLE 6.

Also described herein are media formulations for propagating a graminaceous plant. Examples of media formulations include a callus induction media formulation such as CIM2, CIM3, CIM4, CIM5, and CIM6 as listed in TABLE 1; a suspension culture media formulation including basal medium, 2.5 mg/l ABA, 1000 mg/l proline, and 1000 mg/l myo-inositol; a regeneration media formulation including basal medium, 5 mg/l BA, 1 mg/l 2,4-D, 1000 mg/l proline, and 300 mg/l casein hydrolysate; a shoot multiplication media formulation such as SMM2, SMM3, SMM4, SMM5, SMM6, SMM7, SMM1-2, SMM5-1, and SMM5-2 as listed in TABLES 4 and 5; a shoot quality improvement media formulation including basal medium, and 4 mg/l BA. In the present application, when a concentration is given in milligrams/liter (mg/l) or grams/liter (g/l), the "liter" or "l" means a liter of total composition including active ingredients and inert ingredients. Likewise, if a concentration is given in millimolar (mM), this is based on a total composition including inactive and inert ingredients. "mM" is defined as amount of solute per unit volume of solution. Molar concentration or molarity is most commonly in units of moles of solute per liter of solution. 1 M of any substance has the same number of molecules per liter.

Further described herein is a system for micropropagating graminaceous plants. The system includes at least one sample of immature inflorescence for use as an explant to induce embryogenic calli; at least one step for washing and sterilizing the immature inflorescence; callus induction medium; suspension culture medium; regeneration medium; shoot multiplication medium; rooting medium including activated charcoal; and a plurality of solid media for culturing immature inflorescence and calli. Typically in the system the pH of each medium is 5.5-5.9, and the temperature of each medium is about 23-28° C. For example, the pH of each medium can be 5.7, and the temperature of each medium can be about 25° C. In the system, between about 60,000,000,000 and 750,000,000,000 plants (e.g., between about 350,000,000,000 and 750,000,000,000 plants; or between about 650,000,000,000 and 750,000,000,000 plants; or about 743,008,000,000 plants) are theoretically produced from one single shoot of the graminaceous plants over a one year period. The graminaceous plants can be, for example, *Miscanthus*, transgenic *Miscanthus*, and chromosome-doubled *Miscanthus*, switchgrass, transgenic switchgrass, and other grass plants.

Unless otherwise defined, all technical terms used herein have the same meaning as commonly understood by one of ordinary skill in the art to which this invention belongs.

As used herein, the term "graminaceous plant" means a grass-like plant, with hollow jointed stems and long narrow leaves, having the ability to produce tillers from the bottom of an axillary meristem.

By the term "micropropagation" is the art and science of plant multiplication under aseptic conditions. The process usually includes explant sterilization, callus induction and propagation, plantlet regeneration, shoot multiplication, rooting, and acclamation.

As used herein, the term "large-scale" means on the order of hundreds of thousands to millions, and the term "high-throughput" means the capability to produce plantlets on a large scale in a relatively short time.

The term "about" as used herein when referring to a measurable value such as concentration, time, temperature, etc. is meant to encompass variations of +/−5% of the specified amount.

As used herein the term "plantlet" refers to a young or small plant with roots.

Although media, systems and methods similar or equivalent to those described herein can be used in the practice or testing of the present invention, suitable reagents, systems and methods are described below. All publications, patent applications, and patents mentioned herein are incorporated by reference in their entirety. In the case of conflict, the present specification, including definitions, will control. The particular embodiments discussed below are illustrative only and not intended to be limiting.

DETAILED DESCRIPTION

Figure 1:
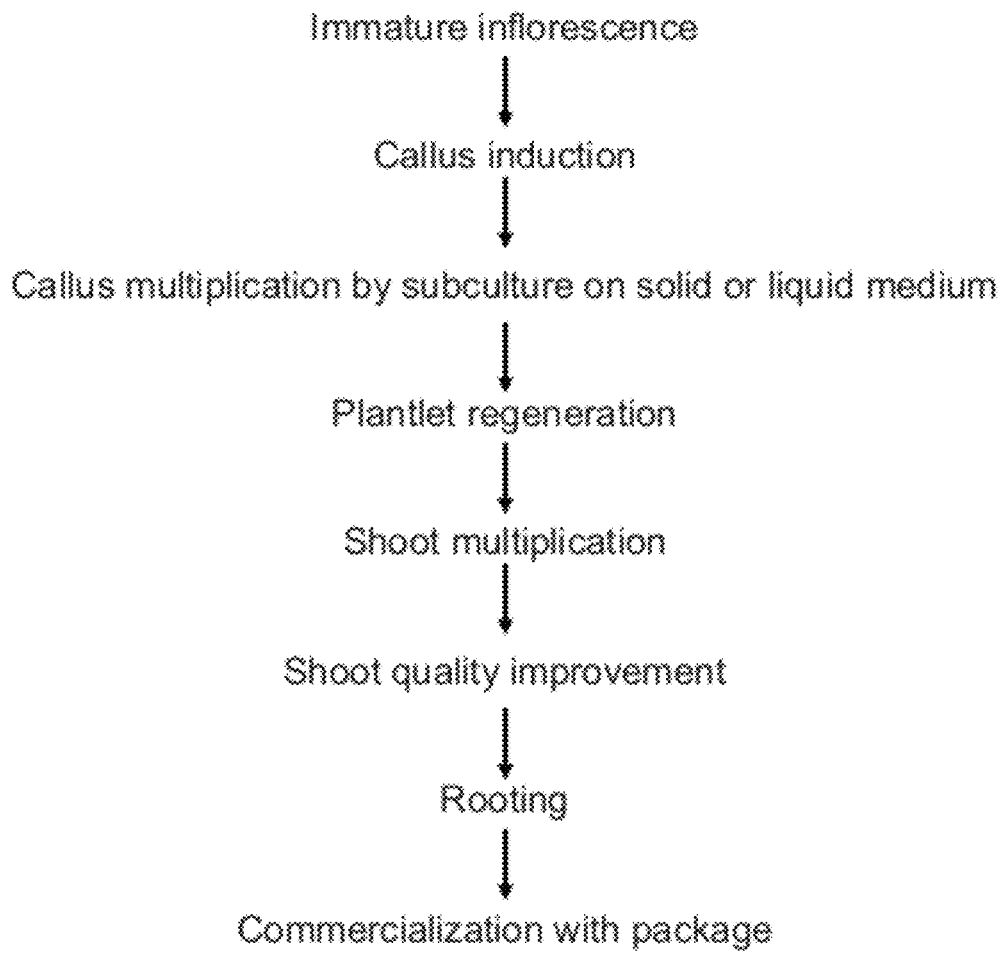
FIG. 1 is a flow chart of a micropropagation method described herein.

Described herein are novel media formulations, methods and systems for micropropagating *M.×giganteus* and other graminaceous plants. These formulations, methods and systems provide several advantages, including ease of obtaining a large amount of starting material with callus induction from immature inflorescence, ease of maintenance of embryogenic calli in medium for a long period of time, no contamination or low levels of contamination observed compared with materials derived from apical meristem and node tissues, a high shoot multiplication rate (which is more than twice that reported by others), high plant quality with 99-100% survival in the greenhouse and the field, and the plant regrowth following a harsh winter in the field. The micropropagation systems, formulations and methods described herein can be used for micropropagation of any graminaceous grasses, such as *Miscanthus* spp. and their transgenic plants and progeny, or chromosome-doubled *Miscanthus* plants, switchgrass and its transgenic plants and progeny, other grass plants, etc. Referring to FIG. 1, this flow chart shows a typical protocol for micropropagation of *M.×giganteus* plants as described herein.

Plant Culture Methods

Methods involving conventional plant and plant cell culture techniques are described herein. Such techniques are generally known in the art and are described in detail in methodology treatises such as Plant Tissue Culture, by Margit Laimer and Waltraud Rucker, 2003, 1$^{st}$ ed., Springer, New York, N.Y.; and Plant Cell Culture: Essential Methods, by Michael R. Davey and Paul Anthony, 2010, Wiley, Hoboken, N.J. Also see, for example, US patent application publication no. 2008-0282424 A1 (U.S. patent application Ser. No. 11/800,719) and PCT application no. WO2010/011717, each incorporated herein by reference.

Methods of Large-Scale Propagation of Plants

Described herein are highly efficient methods for large-scale and high-quality micropropagation of graminaceous plants such as *Miscanthus×giganteus*. A method of propagating a graminaceous plant typically includes the steps of: using immature inflorescence as explants to induce embryogenic calli; performing callus multiplication in liquid suspension medium or on solid medium; regenerating plantlets from embryogenic calli on regeneration medium (RM); culturing the plantlets in liquid shoot multiplication media (SMM) for shoot multiplication resulting in an increased number of shoots; culturing the plantlets in liquid shoot quality improvement media (SQM) for shoot quality improvement resulting in a further increased number of shoots and improvement of shoot quality; and transferring the plantlets to liquid rooting medium including activated charcoal. As mentioned above, any graminaceous grass can be micropropagated on a large scale, e.g., *Miscanthus*, transgenic *Miscanthus*, and chromosome-doubled *Miscanthus* or switchgrass, and its transgenic plants. The step of using immature inflorescence as explants to induce embryogenic calli can include washing, sterilizing, and culturing the immature inflorescence in a callus induction medium (CIM) such as CIM2, CIM3, CIM4, CIM5, or CIM6, the compositions of which are listed in TABLE 1. The step of performing callus propagation can include culturing induced calli from the step of using immature inflorescence as explants to induce embryogenic calli in suspension culture medium (SCM) (e.g., SCM4). In the method, the RM is typically RM4, the liquid SMM is typically one of: SMM2, SMM3, SMM4, SMM5, SMM6, and SMM7, and the liquid SQM is generally SQM4. The compositions of these specific RMs, SMMs and SQMs are listed in TABLES 3, 4 and 6, respectively. A plant (e.g., a young plant, plantlet) produced by this method, as well as one or more progeny thereof, are also described herein.

In one example of a method of large-scale propagation of plants such as *Miscanthus×giganteus* and switchgrass, the following steps are followed. Immature inflorescence is used as explants to induce embryogenic calli. The immature influorescence is typically washed and sterilized, dissected, and placed on CIM containing 2,4-D (2,4-dichlorophenoxy-acetic acid), 6-benzylaminopurine (BA), glutamine, proline, casein hydrolysate, and cysteine to induce embryogenic calli in the dark for about one month (e.g., 25, 26, 27, 28, 29, 30, 31, 32, 33, 34, 35 days). Callus propagation is carried out in liquid suspension medium or on solid medium. Typically, calli induced or subcultured on callus induction medium is transferred to suspension culture medium (SCM) containing abscisic acid (ABA), proline, and myo-inositol for approximately one month (e.g., 25, 26, 27, 28, 29, 30, 31, 32, 33, 34, 35 days) for quick growth and callus quality improvement. In addition, the calli propagated in SCM receive fresh medium every two weeks (i.e., the medium is replaced every two weeks). The time for medium replacement can be adjusted if appropriate, for example, replacement every 12 to 16 days or 10 to 18 days. Plantlet regeneration from embryogenic calli is carried out on RM. In a typical method, multiplied calli are transferred to RM containing BA, 2,4-D, proline and casein hydrolysate and cultured for about one month under light, and can be done in the range of 25-35 days, resulting in plantlets. Next, shoot multiplication is induced. This is generally carried out by culturing shoots in SMM containing BA, indole-3-acetic acid (IAA), and indole-3-butyric acid (IBA) for about one month (e.g., 25, 26, 27, 28, 29, 30, 31, 32, 33, 34, 35, 36, 37, 38, 39, 40 days) under light, and at a temperature of about 23-28° C., resulting in an increased number of shoots at the average of 12 shoots from one single shoot and in the range from 10 to 16 shoots. A shoot quality improvement step is then performed. In this step, shoots are cultured in liquid SQM containing liquid MS basal medium with vitamins and BA for approximately 30 days (e.g., 25, 26, 27, 28, 29, 30, 31, 32, 33, 34, 35 days), resulting in a further increased number of shoots (e.g., in the range of 5-9 shoots) and an increase in shoot diameter (e.g., by 20-75%). Finally, roots are induced from shoots after SQM culture. In this step, one or more individual shoots are transferred to a culture vessel containing liquid rooting medium with activated charcoal for about 15-20 days, resulting in plantlets with healthy and strong roots. In a typical embodiment, the pH for the liquid media formulations described herein is 5.7, but can be in the range of 5.5-5.9, and the culture temperature is typically around 25° C., but can be in the range of about 23-28° C. However, the media formulations described herein may have any suitable pH and temperature for the particular culturing step being performed. In the experiments described below, calli and plantlets were generally exposed to dark and light at the range of 25-40 $\mu$mol/m$^2$/s, respectively.

A *Miscanthus* plant propagated by the methods described herein may be any variety, species and/or clone of *Miscanthus* including, but not limited to, *Miscanthus×giganteus*, *Miscanthus sinensis*, *Miscanthus×ogiformis*, *Miscanthus floridulus*, *Miscanthus transmorrisonensis*, *Miscanthus oligstachyus*, *Miscanthus sacchariflorus*, *Miscanthus×giganteus* 'Amuri', *Miscanthus×giganteus* 'Nagara', *Miscanthus sinensis* var. 'Goliath', *Miscanthus sinensis* var. *gracillimus*, *Miscanthus sinensis* var. *variegates*, *Miscanthus sinensis* var. *purpurascens*, *Miscanthus sinensis* var. *Malepartus*, *Miscanthus sinensis* var. 'Silberfedher' (aka. Silver Feather), *Miscanthus* var. 'Alexander', *Miscanthus* var. 'Adagio', *Miscanthus* var. 'Autumn Light', *Miscanthus* var. 'Cabaret', *Miscanthus* var. 'Condensatus', *Miscanthus* var. 'Cosmopolitan', *Miscanthus* var. 'Dixieland', *Miscanthus* var. 'Gilded Tower', *Miscanthus* var. 'Gold Bar', *Miscanthus* var. 'Gracillimus', *Miscanthus* var. 'Graziella' *Miscanthus* var. 'Grosse Fontaine', *Miscanthus* var. 'Hinjo aka Little Nicky'™, *Miscanthus* var. 'Juli', *Miscanthus* var. 'Kaskade', *Miscanthus* var. 'Kirk Alexander', *Miscanthus* var. 'Kleine Fontaine', *Miscanthus* var. 'Kleine Silberspinne' (aka. 'Little Silver Spider'), *Miscanthus* var. 'Little Kitten', *Miscanthus* var. 'Little Zebra', *Miscanthus* var. 'Lottum', *Miscanthus* var. 'Malepartus', *Miscanthus* var. 'Morning Light', *Miscanthus* var. 'Mysterious Maiden', *Miscanthus* var. 'Nippon', *Miscanthus* var. 'November Sunset', *Miscanthus* var. 'Parachute', *Miscanthus* var. 'Positano', *Miscanthus* var. 'Puenktchen' (aka 'Little Dot'), *Miscanthus* var. 'Rigoletto', *Miscanthus* var. 'Sarabande', *Miscanthus* var. 'Silberpfeil' (aka. Silver Arrow), *Miscanthus* var. 'Silverstripe', *Miscanthus* var. 'Super Stripe', *Miscanthus* var. 'Strictus', or *Miscanthus* var. 'Zebrinus'. In some embodiments, a plant propagated by the methods described herein can be a hybrid of different species, varieties of a specific species, or clones of a variety.

As mentioned above, the methods described herein provide a number of advantages. For example, using the method as described herein, the theoretical production capacity is 743,008,000,000 plants from one single shoot over one year period. As another example, embryogenic calli can be maintained in medium for long periods of time, which provides for easy maintenance (e.g., keep calli on callus induction medium in the dark and subculture every 6 weeks); the calli retain their regeneration abilities for at least one year; the embryogenic calli have a high multiplication rate; and one is able to obtain large amounts of embryogenic calli and large numbers of plants in a relatively short period of time (e.g., two months). Another example is the use of immature inflorescence and the lower degree of contamination associated with immature inflorescence compared to contamination levels associated with apical meristem and node tissues. The immature inflorescence is not directly exposed to the outside environment conditions and is aseptic, in contrast to node tissues, which are directly exposed to the outside environments or only have one layer of sheath. The apical meristem is a tiny issue inside many immature leaves, and is very difficult to obtain in large quantities. Furthermore, a large quantity of tissues can be obtained from immature inflorescence. For example, a large quantity of tissues can be obtained from a 3-10 cm-long piece of immature inflorescence by cutting it into 0.5 cm pieces and culturing them on callus induction medium.

Media Formulations

Described herein are novel media formulations for large-scale propagation of a graminaceous plant such as *Miscanthus×giganteus* or switchgrass. These media formulations include callus induction media (CIM), suspension culture media (SCM), regeneration media (RM), shoot multiplication media (SMM), shoot quality improvement media (SQM), and rooting media. Exemplary embodiments of these media formulations are shown in TABLES 1-6. Each of the novel media formulations listed in these tables (except where noted) was made using MS basal medium commercially available from PhytoTechnology Laboratories (Shawnee Mission, Kans.) (Murashige T and Skoog F, Physiol Plant 15: 473-497, 1962). Although the experiments described herein involved the use of MS basal medium, any suitable basal medium can be used. Each novel media formulation may include an MS basal medium which itself includes or to which has been added sucrose and/or vitamins. The callus induction media (CIM) formulations of TABLE 1, for example, include MS basal medium with MS vitamins and sucrose (e.g., 20-35 g/l of sucrose).

Each callus induction medium also contains one or more of the following: an auxin, a cytokinin, proline and/or hydroxyproline, a magnesium ion source, amide nitrogen, cysteine or methionine and/or dithiothreitol or other reducing agent, and an amino acid mixture.

In a CIM formulation, an auxin at a concentration of 1-20 mg/l (e.g., 1-19 mg/l, 2-18 mg/l, 3-17 mg/l, 4-16 mg/l, 5-15 mg/l, 6-14 mg/l, 7-13 mg/l, 8-12 mg/l, 9-11 mg/l, etc.) is typically included. Examples of auxins include 2,4-D, NAA, IAA, and IBA. If 2,4-D is used, it is generally used at a concentration of 1-4 mg/l (e.g., 1-3 mg/l, 2-4 mg/l, 2-3 mg/l, etc.) If NAA is used, generally a concentration of 2-10 mg/l (e.g., 3-9 mg/l, 4-8 mg/l, 5-7 mg/l, 6 mg/l, etc.) of NAA is appropriate. If IAA or IBA is the auxin added to the medium, either IAA or IBA is typically added at a concentration of 4-20 mg/l (5-19 mg/l, 6-18 mg/l, 7-17 mg/l, 8-16 mg/l, 9-15 mg/l, 10-14 mg/l, 11-13 mg/l, 12 mg/l, etc.). A cytokinin can be added at a concentration of 0.01-1.5 mg/l (e.g., 0.05-1.4 mg/l, 0.1-1.3 mg/l, 0.4-1.2 mg/l, 0.5-1.1 mg/l, 0.6-1.0 mg/l, 0.7-0.9 mg/l, mg/l, etc.). Examples of cytokinins include BA (e.g., 0.1-1.5 mg/l, 0.2-1.4 mg/l, 0.3-1.3 mg/l, 0.4-1.2 mg/l, 0.5-1.1 mg/l, 0.6-1.0 mg/l, 0.7-0.9 mg/l, 0.8 mg/l, etc. BA), kinetin (e.g., 0.1-1.5 mg/l, 0.2-1.4 mg/l, 0.3-1.3 mg/l, 0.4-1.2 mg/l, 0.5-1.1 mg/l, 0.6-1.0 mg/l, 0.7-0.9 mg/l, 0.8 mg/l, etc., kinetin), zeatin (0.1-1.0 mg/l, 0.2-0.9 mg/l, 0.3-0.8 mg/l, 0.4- 0.7 mg/l, 0.5-0.6 mg/l, etc., zeatin), isopentenyl adenine (2ip) (0.1-1.0 mg/l, 0.2-0.9 mg/l, 0.3-0.8 mg/l, 0.4-0.7 mg/l, 0.5-0.6 mg/l, etc., 2ip), diphenylurea (e.g., 0.01-0.5 mg/l, 0.02-0.4 mg/l, 0.03-0.3 mg/l, 0.04-0.2 mg/l, 0.05-0.1 mg/l, 0.06-0.09 mg/l, 0.07-0.08 mg/l, etc., diphenylurea) and thidiazuron (e.g., 0.01-0.5 mg/l, 0.02-0.4 mg/l, 0.03-0.3 mg/l, 0.04-0.2 mg/l, 0.05-0.1 mg/l, 0.06-0.09 mg/l, 0.07-0.08 mg/l, etc., thidiazuron). Proline or hydroxyproline can be added at a concentration of 0.1-4000 mg/l (e.g., 0.5-3000 mg/l, 0.7-2000 mg/l, 0.9-1000 mg/l, 1.0-900 mg/l, 1.5-800 mg/l, 2.0-700 mg/l, 2.5-600 mg/l, 3.0-500 mg/l, 3.5-400 mg/l, 4.0-300 mg/l, 4.5-200 mg/l, 5.0-100 mg/l, 5.5-90 mg/l, 6.0-80 mg/l, 6.5-70 mg/l, 7.0-60 mg/l, 7.5-50 mg/l, 8.0-40 mg/l, 8.5-30 mg/l, 9.0-20 mg/l, 9.5-10 mg/l, etc.).

A magnesium ion source is generally added. For example, a magnesium ion source can be added at a concentration of 0-2000 mg/l or 1-500 mg/l, or 0-10 mM or 0.5-9.0 mM. One example of a magnesium ion source is magnesium chloride, which is typically added at a concentration of 0.0-2000 mg/l (e.g., 0.5-2000 mg/l, 0.5-1000 mg/l, 1.0-500 mg/l, 1.5-250 mg/l, 2.0-100 mg/l, 2.5-5 etc.). Another example of a magnesium ion source that can be used in the media formulations described herein is magnesium sulphate (e.g., 0-10 mM, 0.5-10 mM, 0.5-9 mM, 1.0-8 mM, 1.5-7 mM, 2.0-6 mM, 2.5-5 mM, 3.0-4 mM, etc. magnesium sulphate).

An amide nitrogen can be added. For example, an amide nitrogen can be added at a concentration of 0-500 mg/l or 1-400 mg/l, or 0-3.4 mM or 0.1-3.0 mM. Examples of amide nitrogens include glutamine (e.g., 0-500 mg/l, 1-500 mg/l, 1-400 mg/l, 2-300 mg/l, 3-200 mg/l, 4-100 mg/l, 5-50 mg/l, 6-25 mg/l, 7-20 mg/l, 8-15 mg/l, 9-10 mg/l, etc., glutamine) and asparagine (e.g., 0-3.4 mM, 0.1-3.4 mM, 0.1-3.0 mM, 0.2-2.5 mM, 0.3-2.0 mM, 0.4-2.5 mM, 0.5-2.0 mM, 0.6-1.5 mM, 0.7-1.0 mM, 0.8-0.9 mM, etc. asparagine). When cysteine is included, it is generally included at a concentration of 0-100 mg/l (e.g., 1-90 mg/l, 1-100 mg/l, 10-80 mg/l, 20-70 mg/l, 30-60 mg/l, 40-50 mg/l, 45 mg/l, etc.). Instead of cysteine, methionine can be added at a concentration of 0-0.8 mM (e.g., 0.2-0.8 mM, 0.2-0.7 mM, 0.3-0.6 mM, 0.4-0.5 mM, etc.). Instead of or in addition to cysteine or methionine, a reducing agent such as dithiothreitol can also be added at a concentration of 0-0.8 mM (e.g., 0.2-0.7 mM, 0.2-0.8 mM, 0.3-0.6 mM, 0.4-0.5 mM, etc.). If an amino acid mixture is included, it is typically added at a concentration of 0.1-1000 mg/l (e.g., 1.0-900 mg/l, 10-800 mg/l, 100-700 mg/l, 200-600 mg/l, 300-500 mg/l, 350-450 mg/l, etc.). An example of an amino acid mixture is casein hydrolysate.

A typical callus induction medium comprises:
1-20 mg/l of an auxin, 0.01-1.5 mg/l of a cytokinin, and 0.1-4000 mg/l of proline or 0.1-4000 mg/l hydroxyproline; and
optionally, one or more selected from the group consisting of:
a magnesium ion source at a concentration of 0.0-2000 mg/l or 0.0-10.0 mM, an amide nitrogen at a concentration of 0-500 mg/l or 0.0-3.4 mM, 0-100 mg/l of cysteine, and 0.1-1000 mg/l of an amino acid mixture.

Another typical callus induction medium comprises:
at least one member selected from the group consisting of:
1-20 mg/l of an auxin, 0.01-1.5 mg/l of a cytokinin, and 0.1-4000 mg/l of proline or 0.1-4000 mg/l hydroxyproline; and
at least one member selected from the group consisting of:
a magnesium ion source at a concentration of 10-2000 mg/l or 0.0-10 mM, an amide nitrogen at a concentration of 10-500 mg/l or 0.0-3.4 mM, 10-100 mg/l of cysteine, and 1-1000 mg/l of an amino acid mixture.

Another typical callus induction medium comprises:
a) 1-4 mg/l 2,4-D;
b) at least one member selected from the group consisting of: 0.1-1.5 mg/l BA and kinetin;
c) 500-4000 mg/l proline; and
d) at least one member selected from the group consisting of 1000-2000 mg/l $MgCl_2.6H_2O$, 100-500 mg/l Glutamine, 50-100 mg/l Cysteine, and 50-1000 mg/l Casein hydrolysate.

Another typical callus induction medium comprises:
a) 2-3.5 mg/l 2,4-D;
b) at least one member selected from the group consisting of: 0.4-1 mg/l BA and kinetin;
c) 1000-3500 mg/l proline; and
d) at least one member selected from the group consisting of: 1000-1500 mg/l $MgCl_2.6H_2O$, 200-400 mg/l Glutamine, 50-60 mg/l Cysteine, and 300-800 mg/l Casein hydrolysate.

The suspension culture media (SCM) formulations of TABLE 2 also include MS basal medium supplemented with MS vitamins and sucrose (e.g., 30 g/l sucrose), as well as 2 mg/l 2,4-D, and 0.5 mg/l BA. In addition, an SCM formulation can include one or more of the following: ABA at a concentration of 0.5-5.0 mg/l (e.g., 1.0-4.0 mg/l, 1.5-3.5 mg/l, 2.0-3.0 mg/l, 2.5 mg/l, etc.), proline and/or hydroxyproline at a concentration of 250-2000 mg/l, (e.g., 300-1500 mg/l, 350-1000 mg/l, 400-900 mg/l, 500-800 mg/l, 600-700 mg/l, etc.), and myo-inositol at a concentration of 100-1500 mg/l (e.g., 200-1400 mg/l, 300-4300 mg/l, 400-1200 mg/l, 500-1100 mg/l, 600-1000 mg/l, 700-900 mg/l, 800 mg/l, etc.). For example, SCM4 includes 2.5 mg/l ABA, 1000 mg/l proline, and 1000 mg/l myo-inositol in addition to MS basal medium supplemented with MS vitamins, sucrose (e.g., 30 g/l sucrose), 2 mg/l 2,4-D, and 0.5 mg/l BA.

A typical suspension culture medium comprises at least one member of the group consisting of:
0.5-5.0 mg/l of ABA,
250-2000 mg/l of proline or 250-2000 mg/l of hydroxyproline, and
100-1500 mg/l of Myo-inositol.

Another typical suspension culture medium comprises:
a) 0.5-5.0 mg/l ABA;
b) 250-2000 mg/l proline or 250-2000 mg/l hydroxyproline; and
c) 100-1500 mg/l myo-inositol.

Another typical suspension culture medium comprises:
a) 2.5-5.0 mg/l ABA;
b) 500-1500 mg/l proline or 500-1500 mg/l hydroxyproline; and
c) 500-1000 mg/l myo-inositol.

The regeneration medium formulations shown in TABLE 3 are made with MS basal medium including vitamins supplemented with sucrose (e.g., 30 g/l sucrose). A typical RM formulation also includes one or more of the following: an auxin, a cytokinin, gibberellins (GA), proline and/or hydroxyproline, a magnesium ion source, cysteine or methionine and/or dithiothreitol or other reducing agent, and an amino acid mixture. A preferred GA is $GA_3$. In an RM formulation, an auxin at a concentration of 0.1-5.0 mg/l (e.g., 0.2-4.0 mg/l, 0.3-3.0 mg/l, 0.4-2.0 mg/l, 0.5-1.0 mg/l, etc.) is typically included. Examples of auxins include 2,4-D, NAA, IAA, and IBA. If 2,4-D is used, it is generally used at a concentration of 0.1-1.0 mg/l (e.g., 0.2-0.9 mg/l, 0.3-0.8 mg/l, 0.4-0.7 mg/l, 0.5-0.6 mg/l, etc.). If NAA is used, generally a concentration of 0.2-3 mg/l (e.g., 0.3-2.5 mg/l, 0.4-2.0 mg/l, 0.5-1.5 mg/l, 0.6-1.0 mg/l, 0.7-0.9 mg/l, 0.8 mg/l, etc.) of NAA is appropriate. If IAA or IBA is the auxin added to the medium, either IAA or IBA is typically added at a concentration of 0.4-5.0 mg/l (e.g., 0.5-4.5 mg/l, 1.0-4.0 mg/l, 1.5-3.5 mg/l, 2.0-3.0 mg/l, 2.5 mg/l, etc.). A cytokinin can be added at a concentration of 0.2-8.0 mg/l (e.g., 0.5-7.5 mg/l, 1.0-7.0 mg/l, 1.5-6.5 mg/l, 2.0-6.0 mg/l, 3.0-5.5 mg/l, 4.0-5.0 mg/l, 4.5 mg/l, etc.). Examples of cytokinins include BA (e.g., 1-8 mg/l, 1.5-7.5 mg/l, 2.0-7.0 mg/l, 2.5-6.5 mg/l, 3.0-6.0 mg/l, 3.5-5.5 mg/l, 4.0-5.0 mg/l, 4.5 mg/l, etc.), kinetin (e.g., 1-8 mg/l, 1.5-7.5 mg/l, 2.0-7.0 mg/l, 2.5-6.5 mg/l, 3.0-6.0 mg/l, 3.5-5.5 mg/l, 4.0-5.0 mg/l, 4.5 mg/l, etc.), zeatin (0.2-4.0 mg/l, 0.5-3.5 mg/l, 1.0-3.0 mg/l, 1.5-2.5 mg/l, 2.0 mg/l, etc.), isopentenyl adenine (2ip) (0.2-4.0 mg/l, 0.5-3.5 mg/l, 1.0-3.0 mg/l, 1.5-2.5 mg/l, 2.0 mg/l, etc.), diphenylurea (e.g., 0.2-2.0 mg/l, 0.5-1.5 mg/l, 1.0 mg/l, etc.) and Thidiazuron 0.2-2.0 mg/l, 0.5-1.5 mg/l, 1.0 mg/l, etc.). GA, such as GA3, can be added at a concentration of 0.1-1.5 mg/l (e.g., 0.2-1.4 mg/l, 0.3-1.3 mg/l, 0.4-1.2 mg/l, 0.5-1.0 mg/l, 0.6-0.9 mg/l, 0.7-0.8 mg/l, etc.). Proline and/or hydroxyproline can be added at a concentration of 500-2000 mg/l (e.g., 600-1900 mg/l, 700-1800 mg/l, 800-1700 mg/l, 900-1600 mg/l, 1000-1500 mg/l, 1100-1400 mg/l, 1200-1300 mg/l, etc.).

A magnesium ion source is generally added. For example, a magnesium ion source can be added at a concentration of 0-750 mg/l or 0.5-650 mg/l, or 0-3.7 mM or 0.5-3.5 mM. One example of a magnesium ion source is magnesium chloride, which can be used at a concentration of 0-750 mg/l (e.g., 0.5-650 mg/l, 0.5-750 mg/l, 1.0-550 mg/l, 1.5-450 mg/l, 2.0-350 mg/l, 2.5-250 mg/l, 3.0-150 mg/l, 3.5-50 mg/l, 5.0-10 mg/l, etc.). Another example of a magnesium ion source that can be used in the media formulations described herein is magnesium sulphate (e.g., 0-3.7 mM, 0.5-3.7 mM, 0.5-3.5 mM, 1.0-3.0 mM, 1.5-2.5 mM, 2.0 mM, etc.).

When cysteine is included, it is generally included at a concentration of 0-75 mg/l (e.g., 1-65 mg/l, 1-75 mg/l, 5-55 mg/l, 10-45 mg/l, 15-35 mg/l, 20-25 mg/l, etc.). Instead of cysteine, methionine can be added at a concentration of 0.0-0.6 mM (e.g., 0.1-0.5 mM, 0.1-0.6 mM, 0.2-0.4 mM, 0.3 mM, etc.). In addition to or instead of cysteine or methionine, a reducing agent such as dithiothreitol can be added at a concentration of 0.0-0.6 mM (e.g., 0.1-0.6 mM, 0.1-0.5 mM, 0.2-0.4 mM, 0.3 mM, etc.). If an amino acid mixture is included, it is typically added at a concentration of 100-500 mg/l (e.g., 150-450 mg/l, 200-400 mg/l, 200-350 mg/l, 250-300 mg/l, etc.). An example of an amino acid mixture is casein hydrolysate.

A typical regeneration medium comprises:
0.1-5.0 mg/l of an auxin, 0.2-8.0 mg/l of a cytokinin, 0.1-1.5 mg/l of GA, and 500-2000 mg/l of a member selected from the group consisting of: proline and hydroxyproline; and optionally, at least one selected from the group consisting of: a magnesium ion source at a concentration of 0.0-750 mg/l or 0.0-3.7 mM, 0.0-75 mg/l of cysteine or methionine, and 100-500 mg/l of an amino acid mixture.

Another typical regeneration medium comprises:
a) 0.1-1.0 mg/l 2,4-D;
b) at least one member selected from the group consisting of: 1-8 mg/l BA, 1-8 mg/l kinetin, 0.2-4.0 mg/l zeatin, 0.2-4.0 mg/l isopentenyl adenine (2ip), 0.2-2.0 mg/ml diphenylurea, and 0.2-2.0 mg/l Thidiazuron;
c) 500-2000 mg/l proline or 500-2000 mg/l hydroxyproline,
d) 0.1-1.5 mg/l GA; and
e) optionally, at least one member selected from the group consisting of: 0.0-750 mg/l $MgCl_2.6H_2O$, 0.0-75 mg/l cysteine, and 100-500 mg/l casein hydrolysate.

Another typical regeneration medium comprises:
a) 0.5-1.0 mg/l 2,4-D;
b) at least one member selected from the group consisting of: 1-5 mg/l BA, 3-5 mg/l kinetin, 0.5-2.0 mg/l zeatin, 0.5-2.0 mg/l isopentenyl adenine (2ip), 0.5-1.0 mg/ml diphenylurea and 0.5-1.0 mg/l Thidiazuron;
c) 1000-1500 mg/l proline or 1000-1500 mg/l hydroxyproline;
d) 1.0-1.4 mg/l GA; and
e) optionally, at least one member selected from the group consisting of 700-800 mg/l $MgCl_2.6H_2O$; 45-55 mg/l Cysteine; and 250-350 mg/l Casein hydrolysate.

As shown in TABLES 4 and 5, shoot multiplication medium (SMM) formulations are made with basal MS medium including sucrose (e.g., 30 g/l sucrose). A typical SMM formulation also includes one or more of the following: IBA, any other auxin, and a cytokinin. If IAA is included as an auxin, it is generally present at a concentration of 0.1-2.0 mg/l (e.g., 0.2-1.8 mg/l, 0.3-1.6 mg/l, 0.4-1.4 mg/l, 0.5-1.2 mg/l, 0.6-1.0 mg/l, 0.7-0.8 mg/l, etc.). If NAA is included as an auxin, it is generally present at a concentration of 0.1-1.5 mg/l (0.2-1.4 mg/l, 0.3-1.3 mg/l, 0.4-1.2 mg/l, 0.5-1.1 mg/l, 0.6-1.0 mg/l, 0.7-0.9 mg/l, 0.8 mg/l, etc.). When IBA is added, it is typically at a concentration of 0.0-1.0 mg/l (e.g., 0.1-0.9 mg/l, 0.1-1.0 mg/l, 0.2-0.8 mg/l, 0.3-0.7 mg/l, 0.4-0.6 mg/l, 0.5 mg/l, etc.). A cytokinin can be added at a concentration of about 0.2-8.0 mg/l (e.g., 0.5-7.5 mg/l, 1.0-7.0 mg/l, 2.0-6.5 mg/l, 3.0-6.0 mg/l, 3.5-5.5 mg/l, 4.0-5.0 mg/l, 4.5 mg/l, etc.). Examples of cytokinins include BA (e.g., 2.0-8.0 mg/l, 2.5-7.5 mg/l, 3.0-7.0 mg/l, 2.5-6.5 mg/l, 3.0-6.0 mg/l, 3.5-5.5 mg/l, 4.0-5.0 mg/l, 4.5 mg/l, etc.), kinetin (e.g., 2.0-8.0 mg/l, 2.5-7.5 mg/l, 3.0-7.0 mg/l, 2.5-6.5 mg/l, 3.0-6.0 mg/l, 3.5-5.5 mg/l, 4.0-5.0 mg/l, 4.5 mg/l, etc.), zeatin (0.5-4.0 mg/l, 1.0-3.5 mg/l, 1.5-3.0 mg/l, 2.0-2.5 mg/l, etc.), isopentenyl adenine (2ip) (0.5-4.0 mg/l, 1.0-3.5 mg/l, 1.5-3.0 mg/l, 2.0-2.5 mg/l, etc.), diphenylurea (e.g., 0.2-2.0 mg/l, 0.5-1.5 mg/l, 1.0 mg/l, etc.) and Thidiazuron (e.g., 0.2-2.0 mg/l, 0.5-1.5 mg/l, 1.0 mg/l, etc.).

A typical shoot multiplication medium comprises one or more of:
0.1-2.0 mg/l of an auxin, and
2.0-8.0 mg/l of a cytokinin.

Another typical liquid shoot multiplication medium comprises:
a) 0.0-1.0 mg/l IBA;
b) at least one member selected from the group consisting of: 0.1-2.0 mg/l IAA and 0.1-1.5 mg/l NAA; and
c) at least one member selected from the group consisting of: 2.0-8.0 mg/l BA, 2.0-8.0 mg/l kinetin, 0.5-4.0 mg/l zeatin, 0.5-4.0 isopentenyl adenine (2ip), 0.2-2.0 mg/l diphenylurea, and 0.2-2.0 mg/l Thidiazuron.

Another typical liquid shoot multiplication medium comprises:
a) 0.1-0.2 mg/l IBA;
b) at least one member selected from the group consisting of: 0.5-1.0 mg/l NAA and 0.4-1.0 mg/l IAA; and
c) at least one member selected from the group consisting of: 3.0-5.0 mg/l BA, 3.0-6.0 mg/l kinetin, 1.0-3.0 mg/l zeatin, 2.0-3.0 isopentenyl adenine (2ip), 0.5-1.5 mg/l diphenylurea, and 0.5-1.5 mg/l Thidiazuron.

As shown in TABLE 6, shoot quality improvement media (SQM) formulations are made with basal MS medium including vitamins. A typical SQM formulation also includes one or more of the following: IBA, any other auxin, and a cytokinin. If IAA is included as an auxin, it is generally present at a concentration of 0.0-2.0 mg/l (e.g., 0.1-1.9 mg/l, 0.1-2.0 mg/l, 0.2-1.8 mg/l, 0.3-1.6 mg/l, 0.4-1.4 mg/l, 0.5-1.2 mg/l, 0.6-1.0 mg/l, 0.7-0.8 mg/l, etc.). If NAA is included as an auxin, it is generally present at a concentration of 0.0-1.0 mg/l (0.1-0.9 mg/l, 0.1-1.0 mg/l, 0.2-0.8 mg/l, 0.3-0.7 mg/l, 0.4-0.6 mg/l, 0.5 mg/l, etc.). When IBA is added, it is typically at a concentration of 0.0-1.0 mg/l (e.g., 0.1-0.9 mg/l, 0.1-1.0 mg/l, 0.2-0.8 mg/l, 0.3-0.7 mg/l, 0.4-0.6 mg/l, 0.5 mg/l, etc.). A cytokinin can be added. Examples of cytokinins include BA (e.g., 1.0-8.0 mg/l, 1.5-7.5 mg/l, 2.0-7.0 mg/l, 2.5-6.5 mg/l, 3.0-6.0 mg/l, 3.5-5.5 mg/l, 4.0-5.0 mg/l, 4.5 mg/l, etc.), kinetin (e.g., 1.0-8.0 mg/l, 1.5-7.5 mg/l, 2.0-7.0 mg/l, 2.5-6.5 mg/l, 3.0-6.0 mg/l, 3.5-5.5 mg/l, 4.0-5.0 mg/l, 4.5 mg/l, etc.), zeatin (0.5-4.0 mg/l, 1.0-3.5 mg/l, 1.5-3.0 mg/l, 2.0-2.5 mg/l, etc.), isopentenyl adenine (2ip) (0.5-4.0 mg/l, 1.0-3.5 mg/l, 1.5-3.0 mg/l, 2.0-2.5 mg/l, etc.), diphenylurea (e.g., 0.2-2.0 mg/l, 0.5-1.5 mg/l, 1.0 mg/l, etc.) and Thidiazuron (e.g., 0.2-2.0 mg/l, 0.5-1.5 mg/l, 1.0 mg/l, etc.).

A typical shoot quality improvement medium comprises:
1.0-8.0 mg/l of a cytokinin; and
optionally 0.0-2.0 mg/l of an auxin.

Another typical shoot quality improvement medium comprises:
a) at least one member selected from the group consisting of: 1.0-8.0 mg/l BA, 1.0-8.0 mg/l kinetin, 0.5-4.0 mg/l zeatin, 0.5-4.0 isopentenyl adenine (2ip), 0.2-2.0 mg/l diphenylurea, and 0.2-2.0 mg/l Thidiazuron;
b) optionally, at least one member selected from the group consisting of: 0.1-2.0 mg/l IAA and 0.1-1.0 mg/l NAA; and
c) optionally, 0.0-1.0 mg/l IBA.

Another typical shoot quality improvement medium comprises:
a) 0.4-0.5 mg/l IAA;
b) 0.1-1 mg/l IBA; and
c) at least one member selected from the group consisting of:
1.0-5.0 mg/l BA, 3.0-6.0 mg/l kinetin, 1.0-3.0 mg/l zeatin, 2.0-3.0 isopentenyl adenine (2ip), 0.5-1.5 mg/l diphenylurea, and
0.5-1.5 mg/l Thidiazuron.

System for Micropropagating Graminaceous Plants

A system for micropropagating graminaceous plants is described herein and includes: at least one sample of immature inflorescence for use as an explant to induce embryogenic calli; the immature inflorescence being suitable for being subjected to at least one step for washing and sterilizing the immature inflorescence; callus induction medium; suspension culture medium; regeneration medium; shoot multiplication medium; rooting medium including activated charcoal; and a plurality of solid media for culturing immature inflorescence and calli. Typically in the system the pH of each medium is 5.5-5.9, and the temperature of each medium is about 23-28° C. For example, in a typical system, the pH of each medium is 5.7, and the temperature for culturing is about 25° C. Theoretically, 743,008,000,000 plants could be produced from one single shoot of the graminaceous plants over a one year period. The system can be used to propagate any graminaceous grass with modifications to the conditions and media formulations described herein. Examples of graminaceous plants that can be propagated on a large scale include *Miscanthus*, transgenic *Miscanthus*, and chromosome-doubled *Miscanthus* or switchgrass and its transgenic plants, and other grass plants. Such a system can be packaged as a kit for commercial use. A kit for micropropagating graminaceous plants would typically include instructions for use and appropriate packaging.

EXAMPLES

The present invention is further illustrated by the following specific examples. The examples are provided for illustration only and should not be construed as limiting the scope of the invention in any way.

Example 1

High-Quality Plantlet Production in *M.×giganteus* Micropropagation

Young leaves and apical meristem tissues were initially used as explants for callus induction, but these failed due to excessive tissue release of phenolic compounds into medium, which caused browning. It was then attempted to obtain aseptic plants from tiller shoots in pots, but this did not succeed due to endogenous microorganisms, resulting in contamination in vitro. Immature inflorescences of *M.×giganteus* were obtained from field-grown material, and washed with tap water and surface-sterilized with 70% ethanol for 1 minute, then washed with double distilled water 3 times. After that, the explants were sterilized with 20% bleach for 20 minutes, and then washed with sterile distilled water 5 times. Under aseptic conditions, the immature inflorescences were dissected, cut to 0.5 cm in length, and placed on CIM. To improve callus quality, BA, glutamine, proline, and casein hydrolysate were added to the novel media formulations, and cysteine was added to prevent callus browning. These novel CIM formulations (CIM2-6) are listed in TABLE 1. TABLE 1 also lists Media "CIM" with typical ingredient ranges, rather than particular values from examples.

TABLE 1

Composition of different CIM.

| Media | 2,4-D (mg/l) | BA (mg/l) | Proline (mg/l) | MgCl$_2$•6H$_2$O (mg/l) | Glutamine (mg/l) | Cysteine (mg/l) | Casein hydrolysate (mg/l) |
|---|---|---|---|---|---|---|---|
| CIM1 | 2.5 | 0 | 0 | 750 | 0 | 0 | 0 |
| CIM2 | 2.5 | 0.5 | 0 | 0 | 0 | 0 | 500 |
| CIM3 | 2.5 | 0.5 | 0 | 0 | 0 | 50 | 0 |
| CIM4 | 2.5 | 0.5 | 2900 | 0 | 0 | 0 | 0 |
| CIM5 | 3.0 | 0 | 2900 | 1350 | 300 | 0 | 500 |
| CIM6 | 2.5 | 0.5 | 1000 | 0 | 0 | 0 | 300 |
| CIM | 1-4 | 0.1-1.5 | 500-4000 | 0-2000 | 0-500 | 0-100 | 50-1000 |

Note:
a) The medium (CIM1) reported by Holme and Petersen (1996) was used as control medium.
b) The basic medium was MS basal medium with vitamin (M519 from PhytoTechnology Laboratories, Shawnee Mission, KS) and 30 g/l sucrose. pH was adjusted to 5.5 before autoclave. Callus induction was carried out in the dark at 25 ± 1° C.

The results showed that all of the novel modified media formulations, formulations CIM2-6, were better than the CIM1 control medium. Calli on the new modified media exhibited less browning, grew better, and were more embryogenic, resulting in calli of higher quality and more readily capable of plant regeneration. Of formulations CIM2-6, CIM6 proved to be the best medium.

A method of suspension culture was developed for callus propagation. In general, suspension cultures result in improved callus growth and quality. *M.×giganteus* callus induction medium, SCM (Holme et al., Plant Cell Tissue Organ Cult 50:203-210, 1997), and switchgrass suspension culture medium were combined to design four novel SCM formulations for *M.×giganteus* callus suspension culture growth. Details of the media are listed in TABLE 2. TABLE 2 also lists Media "SCM" with typical ingredient ranges, rather than particular values from examples.

TABLE 2

Composition of different SCM.

| Media | ABA (mg/l) | Proline (mg/l) | Sorbitol (mM) | Mannitol (mM) | Cysteine (mg/l) | Myo-inositol (mg/l) |
|---|---|---|---|---|---|---|
| SCM1 | 0 | 0 | 100 | 100 | 50 | 0 |
| SCM2 | 0 | 0 | 0 | 0 | 50 | 500 |
| SCM3 | 5.0 | 1000 | 0 | 0 | 0 | 1000 |
| SCM4 | 2.5 | 1000 | 0 | 0 | 0 | 1000 |
| SCM | 0.5-5.0 | 250-2000 | 0 | 0 | 0 | 100-1500 |

Note:
Basal medium was MS basal medium with vitamins supplemented with 30 g/l sucrose, 2 mg/l 2,4-D, and 0.5 mg/l BA, pH 5.7. Suspension culture was carried out in the dark at 26 ± 1° C. with shaking at 130 rpm.

Figure 2:
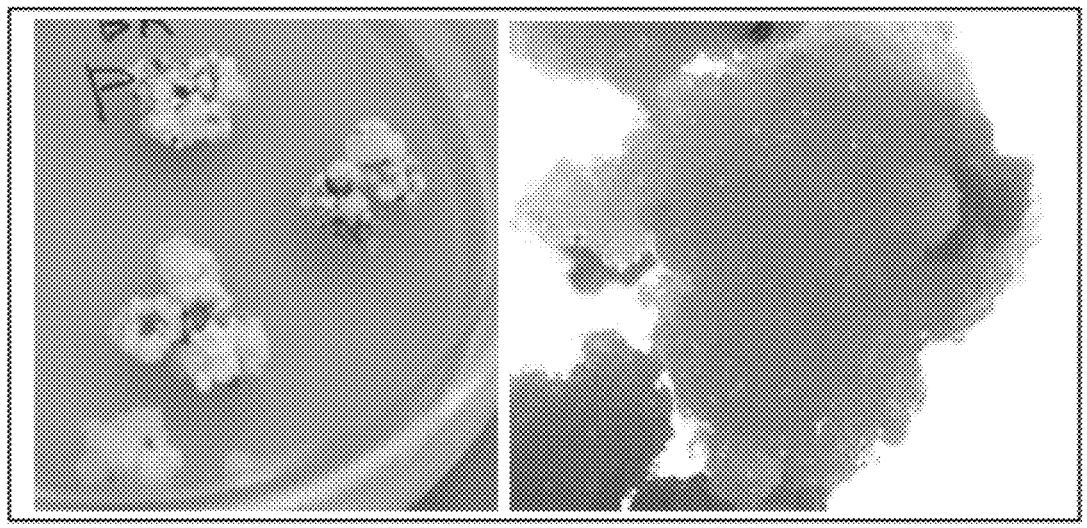
FIG. 2 is a pair of photographs of embryogenic calli induced on callus induction medium (CIM) CIM6.
Figure 3:
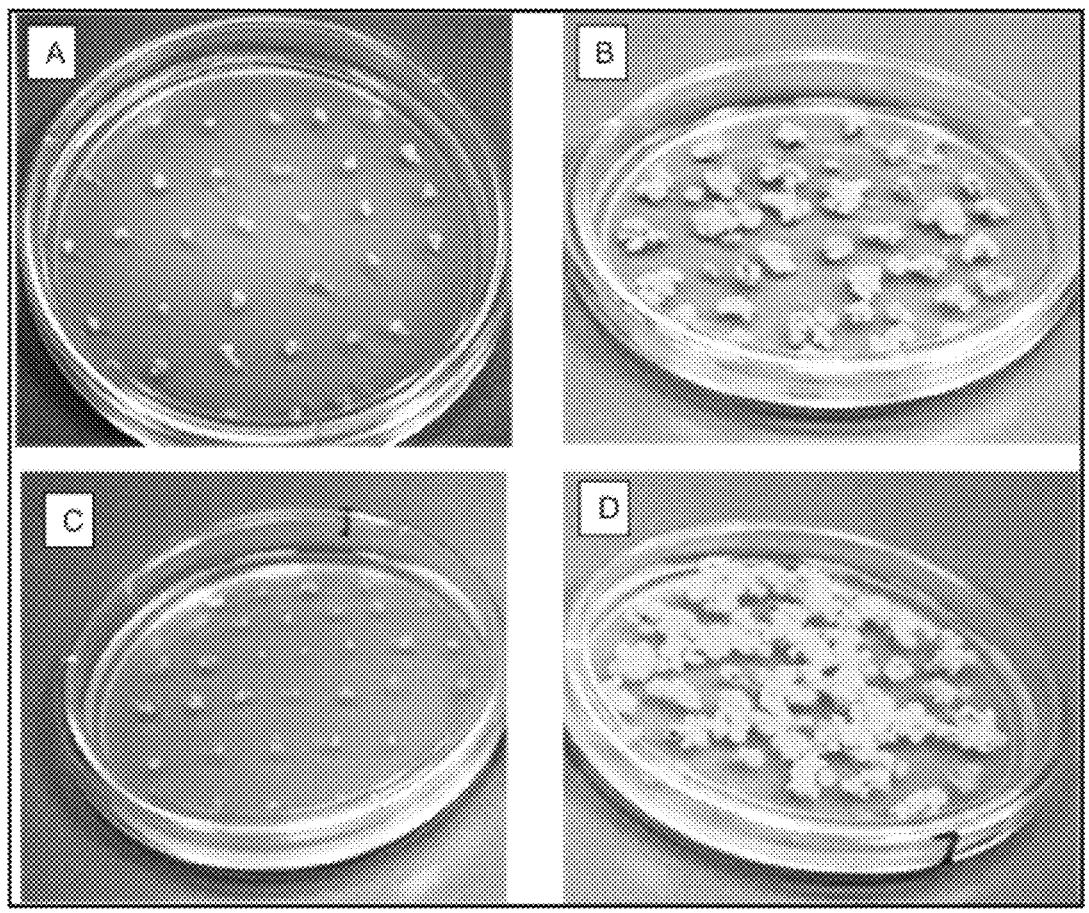
FIG. 3 is a series of photographs showing a comparison of callus growth in solid medium and suspension medium; wherein photograph A shows Calli that were from solid medium (CIM6) and just subcultured; photograph B: shows Calli in plate of photograph A grown for one month; photograph C shows Calli that were from suspension culture medium (SCM) SCM4 and just subcultured on CIM6; and photograph D shows Calli in plate of photograph C grown for one month.

Calli induced or subcultured on CIM6 (FIG. 2) were transferred to suspension culture medium and incubated at 26° C. with shaking at 130 rpm for 4 weeks, with change of liquid medium every two weeks. After that, calli were transferred to CIM6 solid medium. The results showed that calli from suspension culture medium grew faster and exhibited higher embryogenic rates than calli from solid medium. Suspension culture medium 4 (SCM4) was the best SCM for *M.×giganteus* callus growth (FIG. 3) because the calli had about 70% plantlet regeneration rate.

Regeneration Medium (RM) formulations were developed. It is important that calli induced with CIM or multiplied with SCM have the ability to regenerate plants. This ability depends on callus quality and the regeneration medium used. Two media from previous publications were used as control media (RM1 and RM2) (Holme and Petersen, Plant Cell, Tissue and Organ Culture 45:43-52, 1996; Lewandowski, Micropropagation of *Miscanthus×giganteus*. In: Biotechnology in Agriculture and Forest, ed. By Bajaj YPS, Springer-Verlag Berlin Heidelberg. Vol. 39: p 240-255, 1997) and two novel media (RM3 and RM4) were formulated. Details are provided in TABLE 3. TABLE 3 also lists Media "RM" with typical ingredient ranges, rather than particular values from examples.

TABLE 3

Composition of different RM.

| Media | BA (mg/l) | 2,4-D (mg/l) | GA (μM) | Proline (mg/l) | $MgCl_2 \cdot 6H_2O$ (mg/l) | Cysteine (mg/l) | Casein hydrolysate (mg/l) |
|---|---|---|---|---|---|---|---|
| RM1 | 2 | 0 | 0 | 0 | 750 | 0 | 0 |
| RM2 | 1 | 0 | 0 | 0 | 0 | 50 | 0 |
| RM3 | 0 | 0 | 1.4 | 1500 | 750 | 50 | 0 |
| RM4 | 5 | 1 | 0 | 1000 | 0 | 0 | 300 |
| RM | 1-8 | 0.1-1.0 | 0.1-1.5 | 500-2000 | 0-750 | 0-75 | 100-500 |

Note:
A) RM1 and RM2 are disclosed in previous publications and were used as control media.
B) Basal medium was MS basal medium with vitamins supplemented with 30 g/l sucrose, pH 5.8. Plantlet regeneration was conducted in culture incubator with 16 hours light/8 hours dark at 25 ± 1° C.

Calli of approximately 1~1.5 cm in diameter proved optimal and were used. The results showed that RM4 was the best for *M.×giganteus* regeneration. When callus was previously subcultured in CIM6 solid medium, the plantlet regeneration rate was 35%. When callus multiplication was in suspension culture medium (SCM4), the regeneration rate was approximately 70%.

Figure 4:
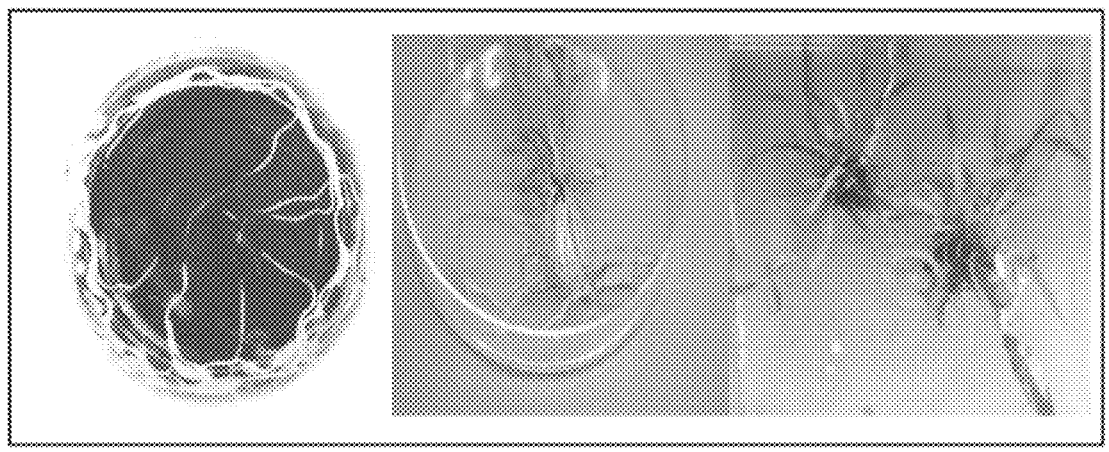
FIG. 4 is a series of photographs showing that activated charcoal (AC) improves *M.×giganteus* root growth in vitro; the picture was taken 10 days after the plantlets were transferred to 0.1% AC medium.

Rooting medium formulations were also developed. Green shoots from regeneration medium transferred to MS medium without hormones grew well. However, the roots grew slowly and became brown, probably due to phenolic compounds secreted from the roots. Activated charcoal (AC) has the ability to absorb toxic compounds in culture medium and improves the growth of plant roots. 0.1% (w/v) AC was added to MS medium without hormones, and excellent root growth was obtained. The roots grew much faster and were a much healthier white color (FIG. 4). The rooting medium contains MS basal medium with MS vitamins and activated charcoal in solid or liquid medium for about 15-20 days.

Micropropagation can be done either by 1) multiplication of somatic embryogenic calli on solid subculture medium or in liquid suspension medium followed by plant regeneration from the calli, or by 2) tillering shoots from apical meristems and nodes i.e. in vitro tillering. In Europe, commercial *M.×giganteus* plants are produced by the second method (Lewandowski, 1997). These two methods were combined to establish a faster and larger-scale propagation system. Based on the callus induction and multiplication in liquid suspension culture medium described above, large amounts of embryogenic calli can be obtained, and large numbers of plantlets easily regenerated from embryogenic calli on regeneration medium in 2 months, using these as starting materials for micropropagation. From the large number of starting material (plantlets), large numbers of plants can be produced with an efficient multiplication power, as described below.

Multiplication rate is a very important parameter, and is required for a commercial micropropagation system. Six different novel shoot multiplication media (SMM) were designed by modifying hormone concentrations, and by adding IBA and AC. The tillering medium reported by Lewandowski (1997) was used as control medium (SMM1) (TABLE 4).

TABLE 4

Shoot multiplication medium (SMM) composition and number of shoots produced from one single shoot on the different media.

| | BA (mg/l) | IAA (mg/l) | IBA (mg/l) | AC (w/v) | No. of shoots | p-value |
|---|---|---|---|---|---|---|
| SMM1 | 3 | 0.45 | 0 | 0 | 4.6 | — |
| SMM2 | 3 | 0.45 | 0 | 0.1% | 4 | 0.6918 |
| SMM3 | 1.5 | 0.45 | 0 | 0 | 6.3 | 0.3823 |
| SMM4 | 3 | 0.25 | 0 | 0 | 4.3 | 0.9093 |
| SMM5 | 5 | 0.45 | 0 | 0 | 9.3 | 0.0433 |
| SMM6 | 3 | 0.45 | 0.1 | 0 | 9 | 0.0406 |
| SMM7 | 3 | 0.45 | 0.5 | 0 | 6.3 | 0.5849 |

Note:
Basal medium: MS medium plus 30 g/l sucrose, pH 5.8. Number of new tillers from single shoots was recorded after one month. Shoots produced in M2 medium had lots of roots, probably due to the added AC in the medium. The p-value was calculated with T-test compared with SMM1 using EXCEL ™ software. Shoot multiplication was carried out in culture incubator with 16 hr light/8 hr dark at 25 ± 1° C.

SMM5 and SMM6 exhibited significantly higher shoot multiplication than control medium (SMM1), being twice that of SMM1. Further experimentation was carried out to confirm the importance of IBA. TABLE 5 provides additional details regarding medium composition and multiplication rate. TABLE 5 also lists Media "SMM" with typical ingredient ranges, rather than particular values from examples.

TABLE 5

Multiplication medium composition and shoot multiplication rate.

| Medium | BA (mg/l) | IAA (mg/l) | IBA (mg/l) | No. of shoots | p-value |
|---|---|---|---|---|---|
| SMM1-1 | 3.0 | 0.45 | 0 | 6.4 | — |
| SMM1-2 | 3.0 | 0.45 | 0.1 | 7.0 | 0.2505 |
| SMM5-1 | 5.0 | 0.45 | 0 | 9.8 | 0.0009 |
| SMM5-2 | 5.0 | 0.45 | 0.1 | 12.3 | 0.00001 |
| SMM8-1 | 3.0 | 1.0 | 0 | 5.5 | 0.1205 |
| SMM8-2 | 3.0 | 1.0 | 0.1 | 4.3 | 0.0280 |
| SMM | 2.0-8.0 | 0.1-2.0 | 0-1.0 | | |

Note:
Basal medium: MS medium plus 30 g/l sucrose, pH 5.8.
Number of new tillers from single shoots was recorded after one month.
The p-value was calculated with T-test compared with SMM1-1 using EXCEL ™ software.
Shoot multiplication was carried out in culture incubator with 16 hr light/8 hr dark at 25 ± 1° C.

From the TABLE 5 data, higher BA (5 mg/l) promoted tillering, and the addition of IBA (0.1 mg/l) enhanced this response (see SMM5-2). The best medium (SMM5-2) produced almost twice as many shoots as control medium (SMM1-1) from one single shoot in one month.

High-quality plantlet production in *M.×giganteus* micropropagation was achieved. Plants from micropropagation in vitro usually have problems with survival when transferred to pots or to the field. This explains why some papers report that plants from micropropagation exhibit lower survival rates compared with plants from rhizome division (Lewandowski 1998). From the experiments described herein, it has been found that shoot quality greatly affects eventual plant quality. In rooting medium, strong shoots produce healthy roots quickly, resulting in plants with higher quality. However, weak or small shoots produce weak roots and lower quality plants. The propagation medium described herein is suitable for the production of large numbers of in vitro shoots, with a multiplication rate of 12 shoots from one single shoot in one month, which is more than twice that reported by Lewandowski (1997). However, it is common that a number of shoots from tillering are weak and cannot produce strong roots. To improve the overall quality of *Miscanthus* plants from micropropagation, which is required for large scale commercial production, it is essential to produce high quality shoots. Therefore, different concentrations of BA-containing media were compared to determine the impact on *Miscanthus* shoot growth and quality.

Materials used were from in vitro grown *Miscanthus* shoots on multiplication medium (SMM5-2). The shoot clusters were separated, and a single shoot was transferred to fresh medium every one month. Similar size shoots were selected for the shoot quality improvement experiment. Five novel media were designed focusing on BA functions without IAA and IBA, as listed in TABLE 6. The growth conditions were 25±2° C. and 16/8 h light/dark light cycle in growth chamber.

TABLE 6

Composition of shoot quality improvement media (SQM).

| Medium | Composition |
|---|---|
| CK | MS + BA 5 mg/l + IAA 0.45 mg/l + IBA 0.1 mg/l |
| SQM1 | MS + BA 1 mg/l |
| SQM2 | MS + BA 2 mg/l |
| SQM3 | MS + BA 3 mg/l |
| SQM4 | MS + BA 4 mg/l |
| SQM | MS + BA (1.0-8.0) + IAA (0-2.0) + IBA (0-1.0) |

Note:
Basal medium: liquid MS with vitamins, pH 5.8.

Figure 5:
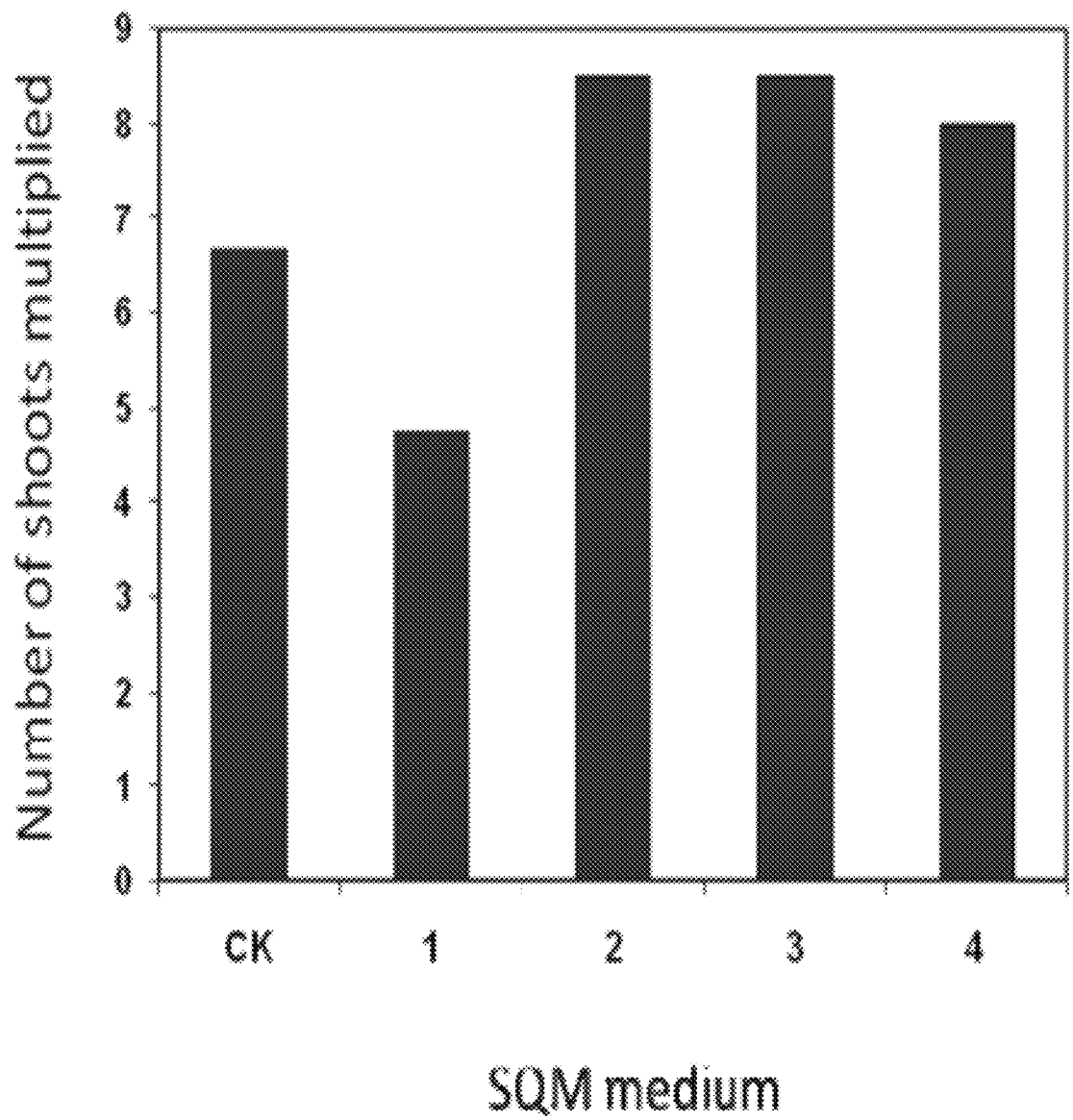
FIG. 5 is a graph showing the effect of shoot quality improvement media (SQM) on number of shoots multiplied.

The number of shoots regenerated, shoot height, and shoot stem diameter data were recorded and analyzed after the 30 days of culture. The results indicated that the number of shoots multiplied was affected by different media (FIG. 5). SQM2 produced significantly more shoots than SQM1, but not with SQM3, SQM4 and control (CK) media. This indicated that the effect of BA (2-4 mg/L) on shoot multiplication was the same as the control.

Figure 6:
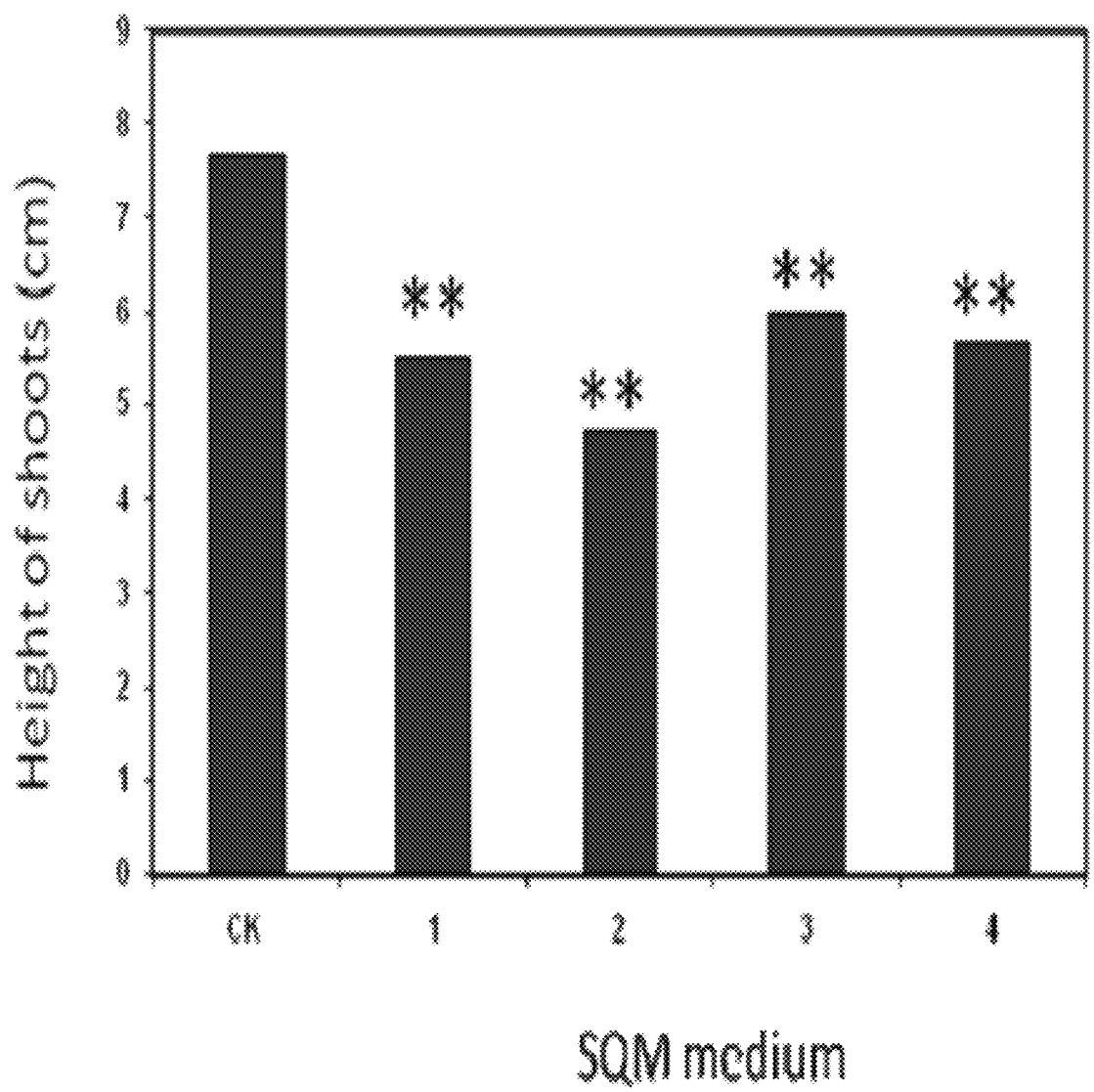
FIG. 6 is a graph showing the effect of SQM on height of shoots.

The height of multiplied shoots was affected by the addition of the plant growth regulators IAA and IBA to the medium (FIG. 6). The control medium (with IAA and IBA) produced longer shoots than SQM1, 2, 3, and 4, and the shoots from SQM2 were the shortest.

Figure 7:
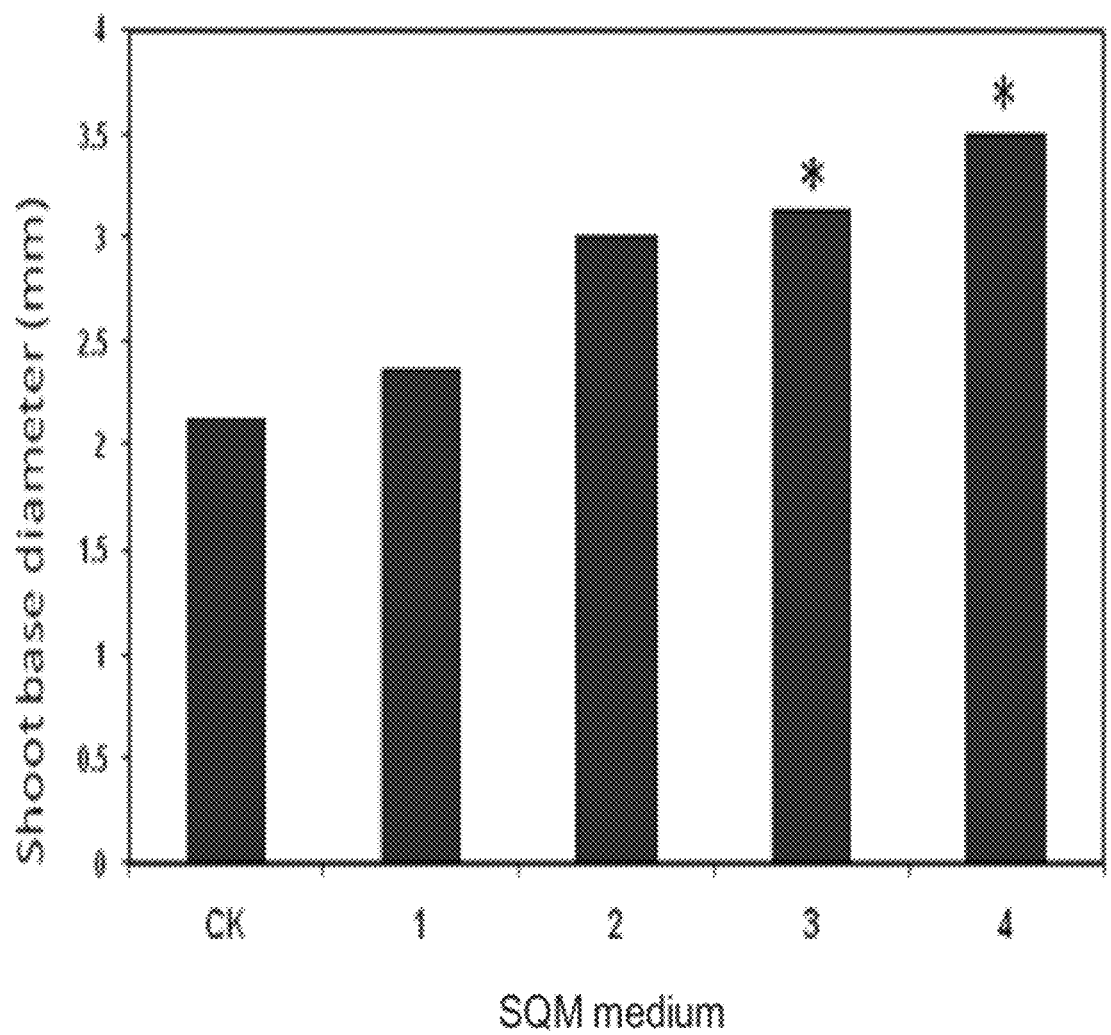
FIG. 7 is a graph showing the effect of SQM on diameter of the shoot base.

The shoot diameter was also affected by different media (FIG. 7). Shoots produced in SQM3 and 4 were significantly thicker at the shoot base than in the control, while SQM1 and 2 were no differences from the control. This indicated that MS medium supplemented with BA 3-4 mg/l could improve shoot quality by increased shoot diameter, perhaps by enhanced sturdiness and vigor.

Figure 8:
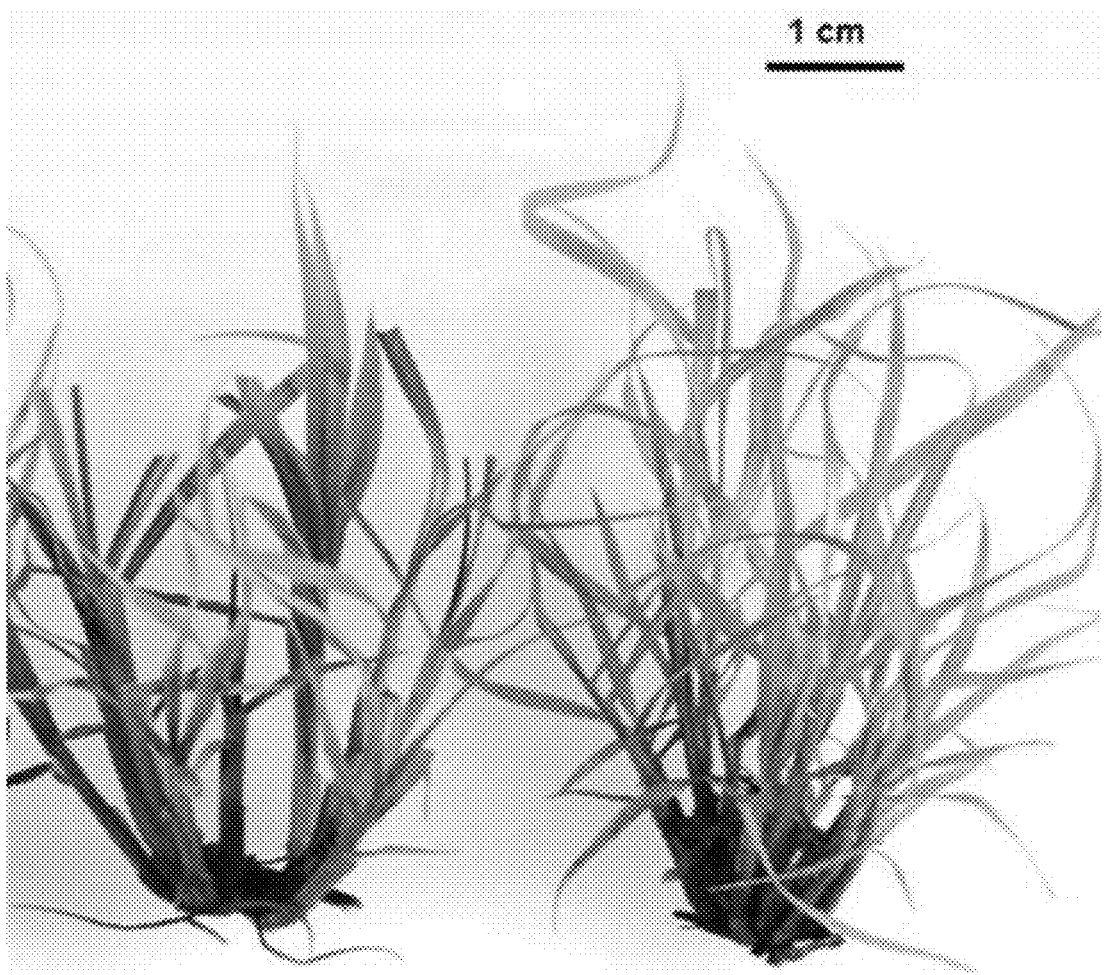
FIG. 8 is a pair of photographs showing that shoot quality was improved in SQM4 for 30 days.
Figure 9:
FIG. 9 is a photograph of *Miscanthus* plantlets produced by the media formulations and methods described herein.
Figure 10:
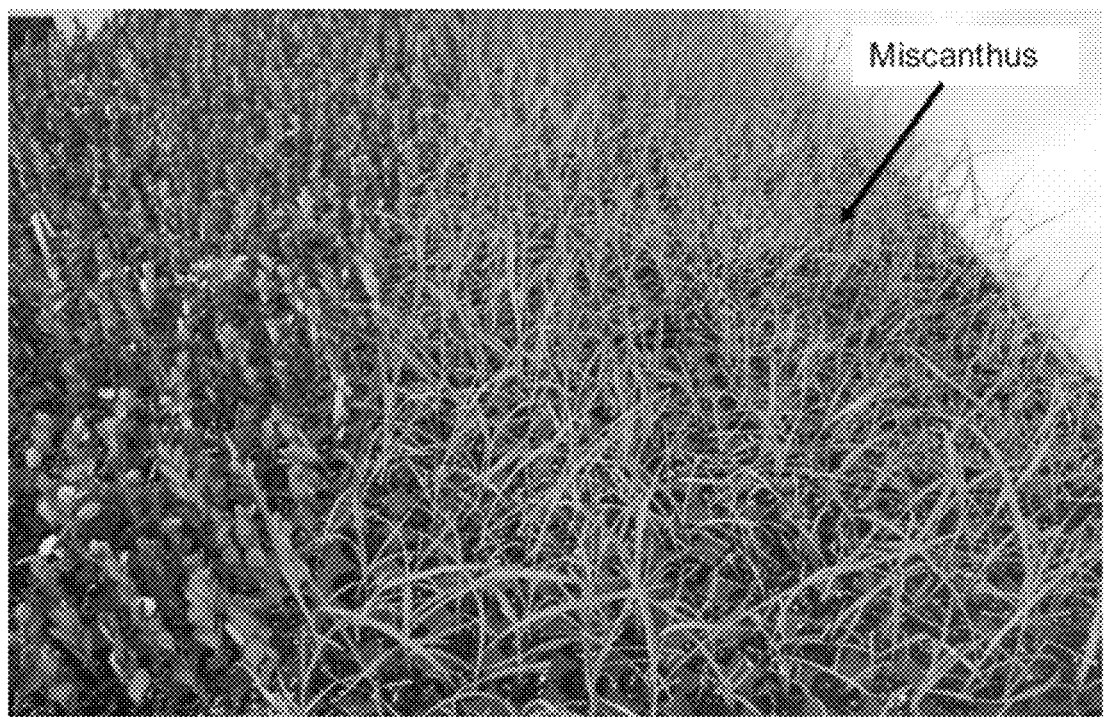
FIG. 10 is a photograph of *Miscanthus* plantlets showing a high survival rate after being transferred to soil plugs in a greenhouse.
Figure 11:
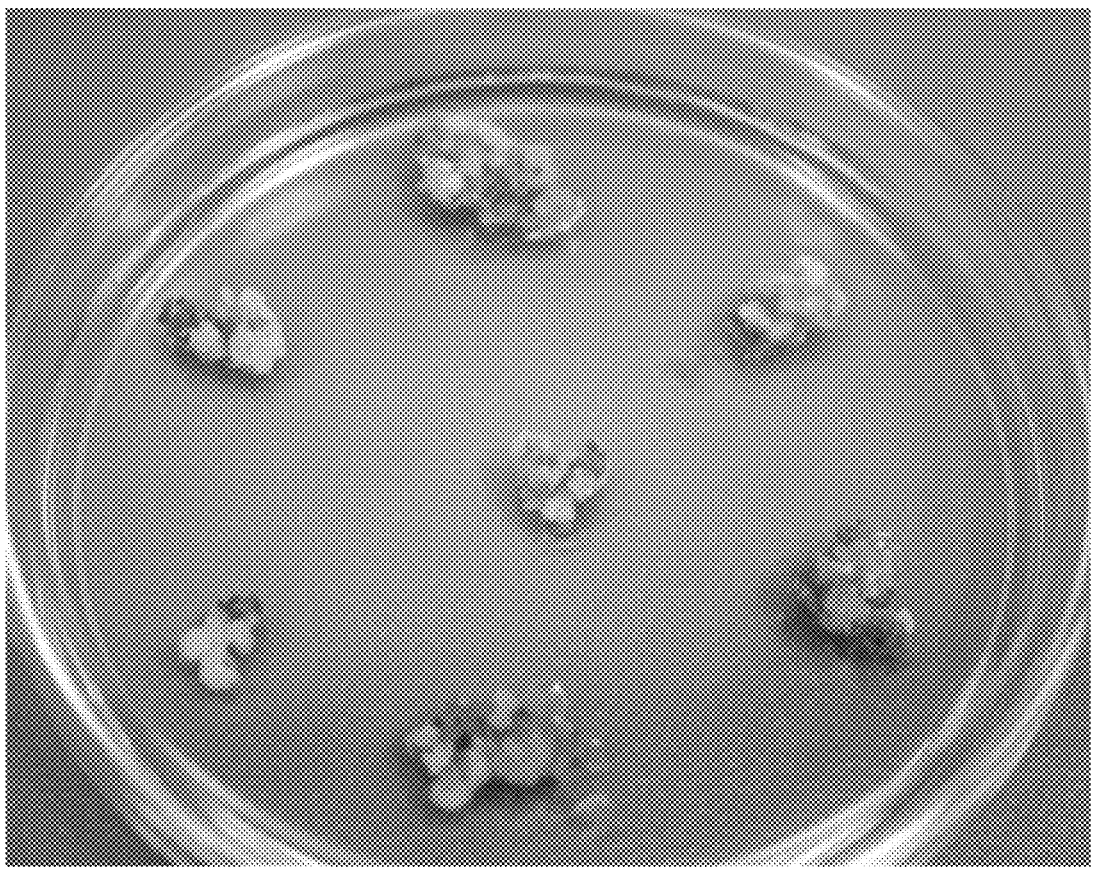
FIG. 11 is a photograph of a culture dish showing plant regeneration from calli propagated in suspension culture medium for one month. Approximately 75% of calli are able to generate plantlets.

Plantlets produced by the improved medium (SQM4) were sturdier than control plants (FIG. 8). The above shoot quality improvement medium (SQM) was designed to enhance shoot rooting and commercial product quality. While SQM is effective in shoot quality improvement, it cannot replace multiplication medium. The proper use of this medium is to add one cycle in SQM4 for shoot quality improvement for 30 days prior to rooting. Products from these shoots showed improved rooting quality and commercial quality potential.

A 99% plant survival was obtained following acclimatization in the greenhouse and transplant in the field. A field trial showed that the plants in the field became established, tolerated the harsh winter and exhibited new growth in the field during the spring of the following year. With the established *Miscanthus* micropropagation system described herein, the theoretical production capacity is 743,008,000,000 plants from one single shoot over one year period (TABLE 7).

TABLE 7

Miscanthus multiplication from one single shoot

| Time | Propagation number |
|---|---|
| Jan | 1 |
| Feb | 12 |
| Mar | 144 |
| Apr | 1,728 |
| May | 20,736 |
| June | 248,832 |
| July | 2,985,984 |
| Aug | 35,831,808 |
| Sept | 429,981,696 |
| Oct | 5,159,780,352 |
| Nov | 61,917,364,224 |
| Dec | 743,008,370,700 |

Other Embodiments

Any improvement may be made in part or all of the reagents and method steps. All references, including publications, patent applications, and patents, cited herein are hereby incorporated by reference. The use of any and all examples, or exemplary language (e.g., "such as") provided herein, is intended to illuminate the invention and does not pose a limitation on the scope of the invention unless otherwise claimed. Any statement herein as to the nature or benefits of the invention or of the preferred embodiments is not intended to be limiting, and the appended claims should not be deemed to be limited by such statements. More generally, no language in the specification should be construed as indicating any non-claimed element as being essential to the practice of the invention. Although the experiments described herein involve micropropagation *Miscanthus×giganteus*, the micropropagation methods and media described herein can be used to propagate additional plants (e.g., switchgrass) on a large-scale.

This invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contraindicated by context.

What is claimed is:

1. A method of propagating a graminaceous plant, the method comprising the steps of:
   a) using immature inflorescence as explants to induce embryogenic calli, wherein step a) comprises washing, sterilizing, and culturing the immature inflorescence in callus induction medium comprising MS basal medium, MS vitamins, 20-35 g/l of sucrose, 1-4 mg/l of 2,4-D, 0.1-1.5 mg/l of BA, 500-4000 mg/l of proline, 0-2000 mg/l of MgCl$_2$, 0-500 mg/l of glutamine, 0-100 mg/l of cysteine, and 50-1000 mg/l of casein;

b) performing callus multiplication in liquid suspension medium or on solid medium to propagate embryogenic calli, wherein step b) comprises culturing induced calli from step a) in a suspension culture medium comprising MS basal medium, MS vitamins, 30 g/l sucrose, 2 mg/l 2,4-D, 0.5 mg/l BA, 0.5-5.0 mg/l of ABA, 250-2000 mg/l of proline, and 100-150 mg/l of myo-inositol;

c) regenerating shoots from the embryogenic calli of step b) on regeneration medium, wherein the regeneration medium comprises MS basal medium, vitamins, 30 g/l sucrose, 1-8 mg/l of BA, 0.1-1.0 mg/l of 2,4-D, 0.1-1.5 µM of GA, 500-2000 mg/l of proline, 0-750 mg/l of MgCl$_2$, 0-75 mg/l of cysteine, and 100-500 mg/l of casein hydrolysate;

d) culturing the shoots in liquid shoot multiplication media for shoot multiplication resulting in an increased number of shoots, wherein the liquid shoot multiplication media comprises MS medium, 30 g/l of sucrose, 2.0-8.0 mg/l of BA, 0.1-2.0 mg/l of IAA, and 0-1.0 mg/l of IBA;

e) culturing the shoots in liquid shoot quality improvement media for shoot quality improvement resulting in a further increased number of shoots and an increase in shoot diameter, wherein the liquid shoot quality improvement media comprises MS medium, vitamins, 1.0-8.0 mg/l of BA, 0-2.0 mg/l of IAA and 0-1.0 mg/l of IBA; and f) transferring the shoots to liquid rooting medium comprising activated charcoal to produce plantlets, wherein the liquid rooting medium comprises MS basal medium, MS vitamins and activated charcoal.

2. The method of claim 1, wherein the graminaceous plant is selected from the group consisting of: switchgrass, transgenic switchgrass, *Miscanthus*, transgenic *Miscanthus*, and chromosome-doubled *Miscanthus*, and other grass plants.

3. A method of large-scale propagation of a graminaceous plant, the method comprising the steps of:

a) culturing graminaceous plant shoots in liquid shoot multiplication media for shoot multiplication resulting in an increased number of shoots, wherein the liquid shoot multiplication media comprises MS medium, 30 g/l of sucrose, 2.0-8.0 mg/l of BA, 0.1-2.0 mg/l of IAA, and 0-1.0 mg/l of IBA;

b) culturing the shoots in liquid shoot quality improvement media for shoot quality improvement resulting in a further increased number of shoots and an increase in shoot diameter; and c) transferring the shoots to liquid rooting medium comprising MS basal medium, MS vitamins and activated charcoal to produce plantlets, wherein the liquid shoot quality improvement media comprises MS medium, vitamins, 1.0-8.0 mg/l of BA, 0-2.0 mg/l of IAA and 0-1.0 mg/l of IBA.

4. The method of claim 3, wherein between about 60,000,000,000 and 750,000,000,000 plants are produced from one single shoot of the graminaceous plants over a one year period.

5. The method of claim 3, wherein between about 350,000,000,000 and 750,000,000,000 plants are produced from one single shoot of the graminaceous plants over a one year period.

6. A method of propagating a graminaceous plant, the method comprising the steps of:

a) using immature inflorescence as explants to induce embryogenic calli;

b) performing callus multiplication in liquid suspension medium or on solid medium to propagate embryogenic calli;

c) regenerating shoots from the embryogenic calli of step b) on regeneration medium comprising MS basal medium, vitamins, 30 g/l sucrose, 1-8 mg/l of BA, 0.1-1.0 mg/l of 2,4-D, 0.1-1.5 µM of GA, 500-2000 mg/l of proline, 0-750 mg/l of MgCl$_2$, 0-75 mg/l of cysteine, and 100-500 mg/l of casein hydrolysate;

d) culturing the shoots in liquid shoot multiplication media for shoot multiplication resulting in an increased number of shoots, wherein the liquid shoot multiplication media comprises MS medium, 30 g/l of sucrose, 2.0-8.0 mg/l of BA, 0.1-2.0 mg/l of IAA, and 0-1.0 mg/l of IBA;

e) culturing the shoots in liquid shoot quality improvement media for shoot quality improvement resulting in a further increased number of shoots and an increase in shoot diameter, wherein the liquid shoot quality improvement media comprises MS medium, vitamins, 1.0-8.0 mg/l of BA, 0-2.0 mg/l of IAA and 0-1.0 mg/l of IBA; and f) transferring the shoots to liquid rooting medium comprising MS basal medium, MS vitamins and activated charcoal to produce plantlets, wherein the graminaceous plants are selected from the group consisting of: *Miscanthus*, transgenic *Miscanthus*, and chromosome-doubled *Miscanthus*, switchgrass, transgenic switchgrass, and other grass plants, wherein step a) comprises washing, sterilizing, and culturing the immature inflorescence in callus induction medium (CIM) comprising MS basal medium, MS vitamins, 20-35 g/l of sucrose, 1-4 mg/l of 2,4-D, 0.1-1.5 mg/l of BA, 500-4000 mg/l of proline, 0-2000 mg/l of MgCl$_2$, 0-500 mg/l of glutamine, 0-100 mg/l of cysteine, and 50-1000 mg/l of casein, wherein step b) comprises culturing induced calli from step a) in a suspension culture medium (SCM) comprising MS basal medium, MS vitamins, 30 g/l sucrose, 2 mg/l 2,4-D, 0.5 mg/l BA, 0.5-5.0 mg/l of ABA, 250-2000 mg/l of proline, and 100-150 mg/l of myo-inositol, and wherein the pH of the callus induction medium, the suspension culture medium, the regeneration medium, the liquid shoot multiplication media, the liquid shoot quality improvement media, and the liquid rooting medium are each 5.5-5.9, and the temperature of each medium is about 23-28° C.

7. The method of claim 3, wherein the graminaceous plant is selected from the group consisting of: *Miscanthus*, transgenic *Miscanthus*, and chromosome-doubled *Miscanthus*.

8. A method of large-scale propagation of a graminaceous plant, the method comprising the steps of:

a) culturing graminaceous plant shoots in liquid shoot multiplication media for shoot multiplication resulting in an increased number of shoots;

b) culturing the shoots in liquid shoot quality improvement media for shoot quality improvement resulting in a further increased number of shoots and an increase in shoot diameter, wherein the liquid shoot quality improvement media comprises MS medium, vitamins, 1.0-8.0 mg/l of BA, 0-2.0 mg/l of IAA and 0-1.0 mg/l of IBA;

c) transferring the shoots to liquid rooting medium comprising MS basal medium, MS vitamins and activated charcoal to produce plantlets;

wherein the liquid shoot multiplication media comprises MS medium, 30 g/l of sucrose, 2.0-8.0 mg/l of BA, 0.1-2.0 mg/l of IAA, and 0-1.0 mg/l of IBA.

9. The method of claim 8, further comprising transplanting the plantlets to a field at an approximately 99%-100% survival rate.

10. A method of large-scale propagation of a graminaceous plant, the method comprising the steps of:
   a) culturing graminaceous plant shoots in liquid shoot multiplication media for shoot multiplication resulting in an increased number of shoots,
   wherein the liquid shoot multiplication media comprises MS medium, 30 g/l of sucrose, 2.0-8.0 mg/l of BA, 0.1-2.0 mg/l of IAA, and 0-1.0 mg/l of IBA;
   b) culturing the shoots in liquid shoot quality improvement media for shoot quality improvement resulting in a further increased number of shoots and an increase in shoot diameter,
   wherein the liquid shoot quality improvement media comprises MS medium, vitamins, 1.0-8.0 mg/l of BA, 0-2.0 mg/l of IAA and 0-1.0 mg/l of IBA; and
   c) transferring the shoots to liquid rooting medium comprising MS basal medium, MS vitamins and activated charcoal to produce plantlets,
   wherein the graminaceous plant is selected from the group consisting of: *Miscanthus*, transgenic *Miscanthus*, and chromosome-doubled *Miscanthus*.

11. The method of claim 8, wherein between about 60,000,000,000 and 750,000,000,000 plants are produced from one single shoot of the graminaceous plants over a one year period.

12. The method of claim 8, wherein between about 350,000,000,000 and 750,000,000,000 plants are produced from one single shoot of the graminaceous plants over a one year period.

13. The method of claim 8, wherein the graminaceous plant is selected from the group consisting of: *Miscanthus*, transgenic *Miscanthus*, and chromosome-doubled *Miscanthus*.

* * * * *